(12) United States Patent
Baylink et al.

(10) Patent No.: US 9,850,499 B2
(45) Date of Patent: Dec. 26, 2017

(54) VECTORS AND METHODS FOR THE EFFICIENT GENERATION OF INTEGRATION/TRANSGENE-FREE INDUCED PLURIPOTENT STEM CELLS FROM PERIPHERAL BLOOD CELLS

(71) Applicant: Loma Linda University, Loma Linda, CA (US)

(72) Inventors: David J. Baylink, Redlands, CA (US); Kin-Hing William Lau, Redlands, CA (US); Xiaobing Zhang, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

(21) Appl. No.: 15/261,803

(22) Filed: Sep. 9, 2016

(65) Prior Publication Data

US 2017/0009252 A1 Jan. 12, 2017

Related U.S. Application Data

(63) Continuation of application No. 14/157,944, filed on Jan. 17, 2014, now abandoned, which is a continuation of application No. PCT/US2013/042115, filed on May 21, 2013.

(60) Provisional application No. 61/817,135, filed on Apr. 29, 2013, provisional application No. 61/650,318, filed on May 22, 2012.

(51) Int. Cl.
*C12N 15/85* (2006.01)
*C12N 5/074* (2010.01)
*C07K 14/47* (2006.01)

(52) U.S. Cl.
CPC .......... *C12N 15/85* (2013.01); *C07K 14/4702* (2013.01); *C07K 14/4747* (2013.01); *C12N 5/0696* (2013.01); *C07K 2319/92* (2013.01); *C12N 2501/48* (2013.01); *C12N 2501/602* (2013.01); *C12N 2501/603* (2013.01); *C12N 2501/604* (2013.01); *C12N 2510/00* (2013.01); *C12N 2820/007* (2013.01); *C12N 2830/48* (2013.01); *C12N 2830/60* (2013.01)

(58) Field of Classification Search
None
See application file for complete search history.

(56) References Cited

U.S. PATENT DOCUMENTS 7,259,011 B2 8/2007 Lucas et al.
8,865,467 B2 10/2014 Mostoslavsky et al.

2011/0064701 A1 3/2011 Young et al.
2011/0236966 A1 9/2011 Mostoslavsky et al.
2012/0009676 A1 1/2012 Mack
2014/0134143 A1 5/2014 Baylink et al.

FOREIGN PATENT DOCUMENTS

| WO | WO 99/45100 | 9/1999 |
| WO | WO 01/10438 | 2/2001 |
| WO | WO 01/87350 | 11/2001 |
| WO | WO 2010/017562 | 2/2010 |
| WO | WO 2011/143343 | 11/2011 |

OTHER PUBLICATIONS

Beverly: "Regulation of Anti-Apoptotic BCL2-Proteins by Non-Canonical Interactions: The Next Step Forward or Two Steps Back?," Journal of Cellular Biochemistry, 2012; 113:3-12.
Della Valle: "The Protein C Pathway and Sepsis," Thrombosis Research, 2012, 129(3): 296-300.
Han, et al. (2011) "Induced Pluripotent Stem Cells: Emerging Techniques for Nuclear Reprogramming", Antioxidant and Redox Signaling, 15(7): 1799-20.
Kohno et al.: "Targeting the Extracellular Signal-Regulated Kinase Pathway in Cancer Thereapy," Biological & Pharmaceutical Bulletin, 2011; 34(12): 1781-84.
Meng, et al.: "Efficient Reprogramming of Human Cord Blood CD34+ Cells Into Induced Pluripotent Stem Cells With OCT4 and SOX2 Alone," www.moleculartherapy.org vol. 20 No. 2, 408-416, Feb. 2012.
Su, et al.: "Efficient Generation of Integration-Free iPS Cells from Human Adult peripheral Blood Using BCL-XL Together with Yamanaka Factors," PLOS ONE / www.plos.one.org May 2013, vol. 8, Issue 5, e64496.
Weber, et al. (2008) "A multi-color panel of novel lentiviral "gene ontology" (LeGO) vectors for functional gene analysis", Molecular Therapy, 16: 698-706 (online version, pp. 1-8).

*Primary Examiner* — Robert M Kelly
(74) *Attorney, Agent, or Firm* — Kilpatrick Townsend & Stockton LLP

(57) ABSTRACT

A vector for generating induced pluripotent stem cells from human target cells comprising a) a vector backbone, b) exactly two, three or four transcription and reprogramming factor genes, each gene separated by a 2a self-cleavage peptide sequence, c) a spleen focus-forming virus promoter, and d) a post-transcriptional regulatory element Wpre, with or without an anti-apoptotic factor gene. A method for generating integration-free induced pluripotent stem cells, the method comprising: a) providing target cells, b) providing one or more than one vector according to the present invention, c) transducing or transfecting the target cells with the one or more than one vector, and d) culturing the transduced or transfected cells in a cell culture, thereby generating integration-free induced pluripotent stem cells.

24 Claims, 19 Drawing Sheets

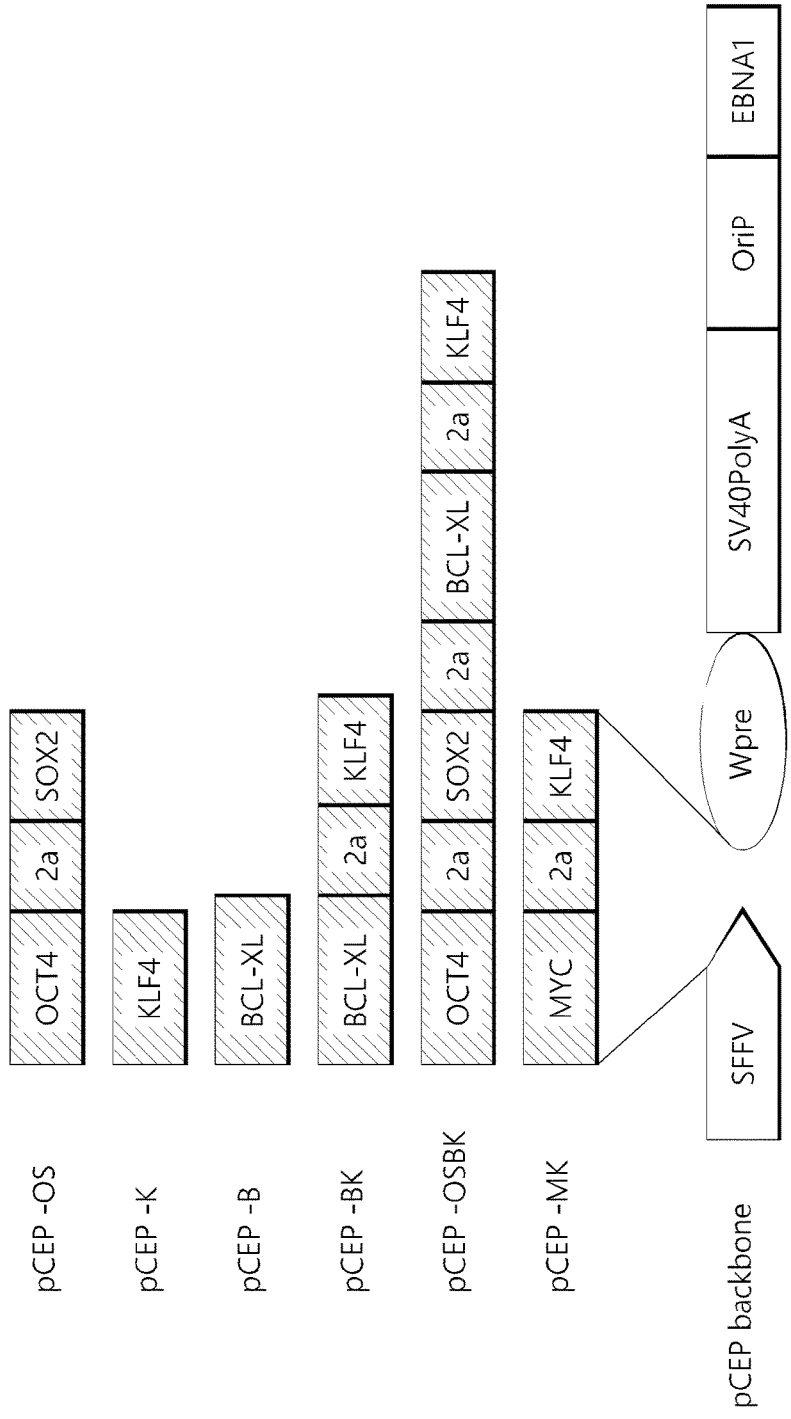
FIG. IIA

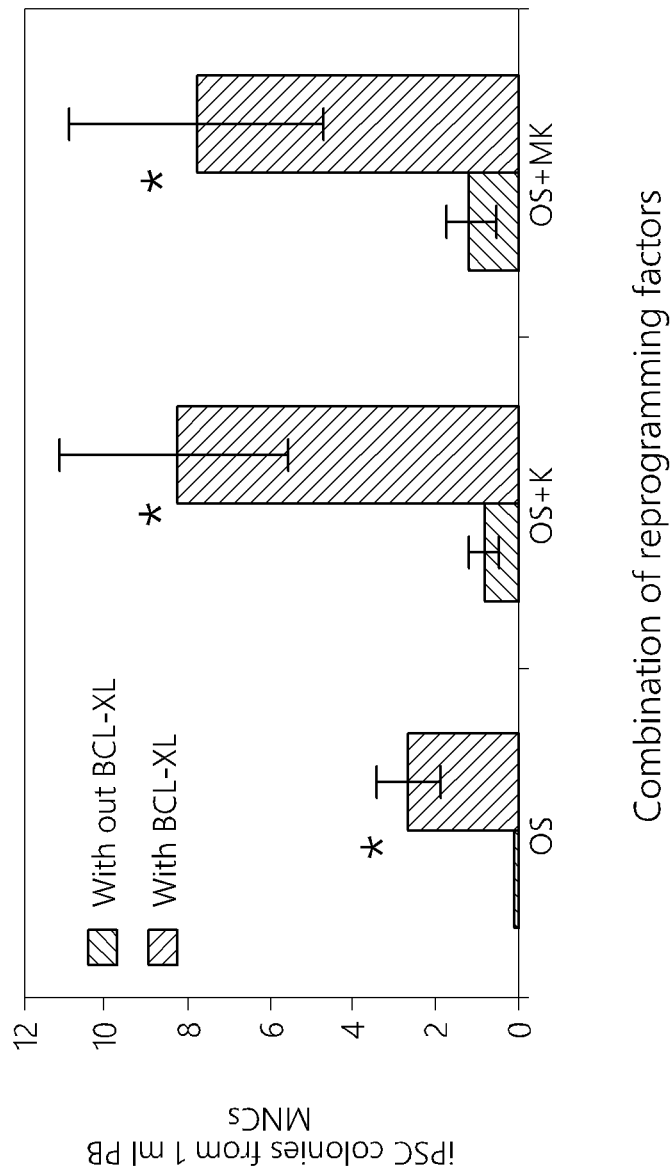
FIG. IIC

VECTORS AND METHODS FOR THE EFFICIENT GENERATION OF INTEGRATION/TRANSGENE-FREE INDUCED PLURIPOTENT STEM CELLS FROM PERIPHERAL BLOOD CELLS

CROSS-REFERENCE TO RELATED APPLICATIONS

The present Application is a continuation U.S. patent application Ser. No. 14/157,944, filed Jan. 17, 2014, which is a continuation of International Patent Application No. PCT/US2013/042115 titled "Vectors and Methods for the Efficient Generation of Integration/Trans gene-Free Induced Pluripotent Stem Cells from Peripheral Blood Cells," filed May 21, 2013, which claims the benefit of United States Provisional Patent Application No. 61/817,135 titled "Efficient Generation of Integration-Free iPS Cells from Human Adult Peripheral Blood Using BCL-XL Together With Yamanaka Factors," filed Apr. 29, 2013; and U.S. Provisional Patent Application No. 61/650,318 titled "Substance and Method for Generating Induced Pluripotent Stem Cells," filed May 22, 2012, the contents of which are incorporated in this disclosure by reference in their entirety.

STATEMENT REGARDING FEDERALLY SPONSORED RESEARCH OR DEVELOPMENT

This invention was made with United States Government support under Basic Award W81XWH-11-1-0607 from the United States Department of Defense, United States Army Medical Research Acquisition Activity (USAMRAA) Grant W81XWH-08-1-0697 from the United States Army Medical Research and Materiel Command (USAMRMC). The United States Government has certain rights in this invention.

BACKGROUND

Induced pluripotent stem cells (iPSCs) that have been generated from somatic cells have a large variety of current and potential uses in regenerative medicine. Among these uses are generating patient-specific cells, tissues and organs for replacement therapy, and for modeling diseases for research.

Induced pluripotent stem cells have been generated from somatic cells such as fibroblasts derived from a skin biopsy by the overexpression of Yamanaka factors (KLF4, MYC, OCT4 and SOX2) or Thomson/Yu factors (LIN28, NANOG, OCT4 and SOX2). Disadvantageously, however, several weeks are required to prepare cells from a skin biopsy for use in generating induced pluripotent stem cells. Further, induced pluripotent stem cells have also been generated from hematopoietic stem cells (progenitor cells) (HSCs) such as CD34+ cells, CD133+ cells, or from unenriched cells such as mononuclear cells (MNCs) that are harvested from bone marrow, cord blood or peripheral blood, and advantageously do not require substantial time to prepare the cells for use in generating induced pluripotent stem cells. Disadvantageously, however, isolating hematopoietic stem cells or CD34+ cells from mobilized peripheral blood and bone marrow is invasive, time-consuming and has potential risks for the donor. Further, generating induced pluripotent stem cells from cord blood cells has only been accomplished only at an efficiency that is too low for widespread clinical use.

Additionally, in some clinical applications, integration/transgene-free induced pluripotent stem cells are preferably used to ameliorate potential adverse effects due to retroviral or lentiviral integration, or due to the interference by residual expression of reprogramming factors during differentiation of induced pluripotent stem cells into progenies. Several methods have been used to produce integration/transgene-free induced pluripotent stem cells, including the use of adenoviruses, artificial chromosome vectors, the Cre/loxP system or excisable polycistronic lentiviral vectors, minicircle DNA, piggyBac transposon, plasmids, protein transduction, the Sendai virus and synthetic modified mRNA. Disadvantageously, however, these methods are associated with very low efficiency of integration/transgene-free induced pluripotent stem cells generation, require repetitive induction or selection, or require virus production. For example, techniques using excisable polycistronic lentiviral vectors and transposons require a separate step to remove the transgenes once reprogramming has been achieved, while using synthetic modified mRNA to produce integration/transgene-free induced pluripotent stem cells requires the daily addition of mRNA by lipofection, and transfection by lipofection is difficult to achieve with some cell types including blood CD34+ cells.

Further, integration/transgene-free induced pluripotent stem cells have been generated from somatic cells using the Epstein-Barr virus (EBV) latent gene-based episomal vector (EBNA1-based episomal vector) that advantageously requires only one transfection of vector DNA by nucleofection for efficient reprogramming, and that is lost in 5% or more of the cells after each cell division, leading to depletion of the vector from cells after long-term passage. Additionally, integration/transgene-free induced pluripotent stem cells have been generated from somatic cells using the pCEP4 vector (that contains the gene coding for the Epstein Barr nuclear antigen (EBNA1) and OriP sequence). Disadvantageously, however, the use of the Epstein-Barr virus (EBV) latent gene-based episomal vector and pCEP4 vector also requires five to seven additional reprogramming factor genes, including strong oncogenes like Myc (c-Myc) (a regulator gene that codes for a transcription factor) or simian virus 40 large T antigen (SV40LT) that might raise safety concerns for general clinical use of the induced pluripotent stem cells generated by using these factors.

The most cost effective approach for generating integration/transgene-free induced pluripotent stem cells from somatic cells is using EV, a plasmid comprising two elements from Epstein-Bar virus (oriP and EBNA1), because there is no need for packaging of viral vectors and one infection is sufficient for successful reprogramming instead of multiple daily infection or the multiple additions of other factors. Binding of the EBNA1 protein to the virus replicon region oriP maintains a relatively long-term episomal presence of the EV plasmids in mammalian cells. These unique features of EV makes it an ideal vector for generating integration/transgene-free induced pluripotent stem cells. EV yields expression of reprogramming factors at sufficiently high levels for several cell divisions, thus allowing for successful reprogramming after only one infection, while the gradual depletion of plasmids during each cell division leads to the generation of integration/transgene-free induced pluripotent stem cells after approximately 2 months of culture.

Among the various cell types used for reprogramming, fibroblasts from skin biopsy or other sources were initially used in many studies for the generation of iPSCs; however, mononuclear cells (MNCs) from peripheral blood (PB) have been widely accepted as a more convenient and almost unlimited resource for cell reprogramming. Peripheral blood mononuclear cells are a mixed population, containing lymphoid cells, including T cells and B cells, and non-lymphoid cells, including myeloid cells, as well as between 0.01% and 0.1% CD34+ hematopoietic stem/progenitor cells (HSCs). In earlier studies, mature T or B cells were efficiently converted to induced pluripotent stem cells with Sendai virus or EV plasmids. However, induced pluripotent stem cells generated from T cells and B cells contain T cell receptor (TRC) or immunoglobulin (IG) gene rearrangements, restricting their broad applications in regenerative medicine. Therefore, attempts to generate integration/transgene-free induced pluripotent stem cells from non-lymphoid cells have been made, however, these attempts generated only between one and five integration-free induced pluripotent stem cells colonies from 1 ml of peripheral blood which is too low for therapeutic use. More recent approaches using factors including EBNA1 and shRNA against TP53 (also known as p53) generate up to ten induced pluripotent stem cells colonies from 1 ml of peripheral blood in non-T cell culture conditions; however, expression of EBNA1 and TP53 shRNA synergistically inhibits the genome guardian p53, which raises concerns about the genomic integrity of induced pluripotent stem cells generated using this approach.

Therefore, there is a need for a vector and method for generating integration-free induced pluripotent stem cells from somatic cells that are not subject to these disadvantages, where the vector and method generate sufficient numbers of integration/transgene-free induced pluripotent stem cells from somatic cells for therapeutic use in a cost-effective manner that does not require the use of excessive number of factors such as TP53 shRNA.

SUMMARY

According to one embodiment of the present invention, there is provided an episomal vector for generating induced pluripotent stem cells from human target cells, the vector comprising: a) an oriP/EBNA1-based plasmid backbone; b) exactly two transcription and reprogramming factor genes, oct4 and sox2, separated by a 2a self-cleavage peptide sequence; c) a spleen focus-forming virus promoter; d) a post-transcriptional regulatory element Wpre; and e) anti-apoptotic factor gene selected from the group consisting of bcl-xl and bcl2.

According to another embodiment of the present invention, there is provided an episomal vector for generating induced pluripotent stem cells from human target cells, the vector comprising: a) an oriP/EBNA1-based plasmid backbone; b) exactly three transcription and reprogramming factor genes, oct4, sox2 and klf4, each separated by a 2a self-cleavage peptide sequence; c) a spleen focus-forming virus promoter; d) a post-transcriptional regulatory element Wpre; and e) anti-apoptotic factor gene selected from the group consisting of bcl-xl and bcl2.

According to another embodiment of the present invention, there is provided an episomal vector for generating induced pluripotent stem cells from human target cells, the vector comprising: a) an oriP/EBNA1-based plasmid backbone; b) exactly four transcription and reprogramming factor genes, oct4, sox2, klf4 and myc, each separated by a 2a self-cleavage peptide sequence; c) a spleen focus-forming virus promoter; d) a post-transcriptional regulatory element Wpre; and e) anti-apoptotic factor gene selected from the group consisting of bcl-xl and bcl2.

According to another embodiment of the present invention, there is provided a vector for generating induced pluripotent stem cells from human target cells, the vector comprising: a) a vector backbone; b) exactly two, three or four transcription and reprogramming factor genes, each gene separated by a 2a self-cleavage peptide sequence; c) a spleen focus-forming virus promoter; and d) a post-transcriptional regulatory element Wpre. In one embodiment, the vector backbone is an oriP/EBNA1-based episomal vector. In another embodiment, the vector backbone is an oriP/EBNA1-based plasmid backbone. In another embodiment, the vector is an episomal vector. In another embodiment, the vector is selected from the group consisting of a plasmid, a non-plasmid, a non-integrating plasmid, a non-integrating vector, a viral vector, a non-integrating viral vector, a self-inactivating vector and a lentivirus vector. In one embodiment, the transcription and reprogramming factor genes are selected from the group consisting of one or more than one Yamanaka factor gene and one or more than one Thomson/Yu factor gene, and a combination of the preceding. In another embodiment, one or more than one of the transcription and reprogramming factor genes are selected from the group consisting of klf4, lin28, myc, nanog, oct4, sox1, sox2, sox3, sox15 and sox18. In another embodiment, a plurality of the transcription and reprogramming factor genes are selected from the group consisting of klf4, lin28, myc, nanog, oct4, sox1, sox2, sox3, sox15 and sox18. In another embodiment, all of the transcription and reprogramming factor genes are selected from the group consisting of klf4, lin28, myc, nanog, oct4, sox1, sox2, sox3, sox15 and sox18. In another embodiment, all of the transcription and reprogramming factor genes are selected from the group consisting of oct4, sox2, klf4 and myc. In another embodiment, the transcription and reprogramming factor genes are exactly two transcription and reprogramming factor genes, oct4 and sox2. In another embodiment, the transcription and reprogramming factor genes are exactly three transcription and reprogramming factor genes, oct4, sox2 and klf4. In another embodiment, the transcription and reprogramming factor genes are exactly four transcription and reprogramming factor genes, oct4, sox2, klf4 and myc. In one embodiment, the 2a self-cleavage peptide sequence is selected from the group consisting of equine rhinitis A virus, foot-and-mouth disease virus, porcine teschovirus-1 and Thosea asigna virus. In another embodiment, the vector further comprises one or more than one gene coding for an inhibitor, siRNA, or shRNA construct of a pro-apoptotic factor. In another embodiment, the vector further comprises one or more than one gene coding for an inhibitor, siRNA, or shRNA construct of a pro-apoptotic factor, where the pro-apoptotic factor is a BAX subfamily pro-apoptotic factor selected from the group consisting of BAK, BAX and BOK. In another embodiment, the vector further comprises one or more than one gene coding for an inhibitor, siRNA, or shRNA construct of a pro-apoptotic factor, where the pro-apoptotic factor is a BH3 subfamily pro-apoptotic factor selected from the group consisting of BAD, BID, BIK, BIML, BLK, BNIP3 and HRK. In another embodiment, the vector further comprises one or more than one anti-apoptotic factor gene encoding one or more than one anti-apoptotic factor. In another embodiment, the vector further comprises one or more than one anti-apoptotic factor gene encoding one or more than one anti-apoptotic factor, where the anti-apoptotic factor is a BCL-2 family anti-apoptotic factor. In another embodiment, the vector further comprises one or more than one anti-apoptotic factor gene encoding one or more than one anti-apoptotic factor, where the anti-apoptotic factor is a BCL-2 family anti-apoptotic factor selected from the group consisting of A1, BCL2, BCL-W, BCL-XL and MCL1. In another embodiment, the vector further comprises one or more than one anti-apoptotic factor gene encoding one or more than one anti-apoptotic factor, where the anti-apoptotic factor is BCL2 or BCL-XL.

According to another embodiment of the present invention, there is provided a method for generating integration-free induced pluripotent stem cells. The method comprises: a) providing target cells; b) providing one or more than one vector to the present invention; c) transducing or transfecting the target cells with the one or more than one vector; and d) culturing the transduced or transfected cells in a cell culture, thereby generating integration-free induced pluripotent stem cells. In one embodiment, the one or more than one vector provided is one vector. In another embodiment, the one or more than one vector provided is a plurality of vectors. In another embodiment, the one or more than one vector provided is two vectors. In another embodiment, the one or more than one vector provided is three vectors. In another embodiment, the one or more than one vector is a first vector and a second vector, and transducing or transfecting the target cells comprising transducing or transfecting the target cells with a first amount of the first vector and a second amount of a second vector, where the first amount is equal to the second amount. In another embodiment, the one or more than one vector is a first vector and a second vector, and transducing or transfecting the target cells comprising transducing or transfecting the target cells with a first amount of the first vector and a second amount of a second vector, where the first amount is half of the second amount. In another embodiment, the one or more than one vector is three vectors. In another embodiment, the one or more than one vector is four vectors. In another embodiment, the one or more than one vector is five vectors. In another embodiment, the one or more than one vector is an episomal vector comprising a strong spleen focus-forming virus promoter, a post-transcriptional regulatory element Wpre, and exactly two transcription and reprogramming factor genes, oct4 and sox2, and the method further comprises transducing or transfecting the target cells with an additional episomal vector comprising a strong spleen focus-forming virus promoter, a post-transcriptional regulatory element Wpre, an anti-apoptotic factor gene bcl-xl, and exactly one transcription and reprogramming factor gene, klf4. In another embodiment, the one or more than one vector is an episomal vector comprising a strong spleen focus-forming virus promoter, a post-transcriptional regulatory element Wpre, and exactly two transcription and reprogramming factor genes, oct4 and sox2, and the method further comprises transducing or transfecting the target cells with a first additional episomal vector comprising a strong spleen focus-forming virus promoter, a post-transcriptional regulatory element Wpre, and exactly one transcription and reprogramming factor gene, klf4, and with a second additional episomal vector comprising a strong spleen focus-forming virus promoter, a post-transcriptional regulatory element Wpre, and an anti-apoptotic factor gene bcl-xl, but without any transcription and reprogramming factor gene. In another embodiment, the target cells are hematopoietic stem cells. In another embodiment, the target cells are peripheral blood mononuclear cells. In another embodiment, the target cells are peripheral blood myeloid cells. In another embodiment, the target cells are peripheral blood cells that have been enriched for one or more than one cell type selected from the group consisting of CD33+ cells, CD34+ cells and CD133+ cells. In another embodiment, the target cells are peripheral blood mononuclear cells that have been enriched for CD33+ cells. In another embodiment, the target cells are peripheral blood cells that have been depleted of cells that express T cell marker CD3 or B cell maker CD19. In another embodiment, the method further comprises harvesting the target cells from a body fluid or tissue. In one embodiment, the body fluid or tissue is selected from the group consisting of bone marrow and cord blood. In another embodiment, the body fluid or tissue is peripheral blood. In another embodiment, the method further comprises providing cord blood, and purifying the cord blood to obtain the target cells. In one embodiment, the cord blood is obtained from a cord blood bank. In another embodiment, the method further comprises enhancing or purifying the target cells for cells that express a CD33 marker. In another embodiment, the method further comprises enhancing or purifying the target cells for cells that express a CD34 marker or a CD133 marker. In another embodiment, the method further comprises depleting the target cells of cells that express a T cell marker CD3 or a B cell maker CD19. In another embodiment, the method further comprises enhancing or purifying the target cells for cells that express a CD33 marker, and depleting the target cells of cells that express a T cell marker CD3 or a B cell maker CD19. In another embodiment, the method further comprises purifying integration-free induced pluripotent stem cells from the cell culture after generating the integration-free induced pluripotent stem cells. In another embodiment, the method further comprises culturing the target cells in a cell culture for a duration of between three days and six days before transducing or transfecting the target cells. In another embodiment, the method further comprises culturing the target cells in a cell culture for a duration of four days before transducing or transfecting the target cells.

According to another embodiment of the present invention, there is provided integration-free induced pluripotent stem cells generated by a method according to the present invention. In one embodiment, the integration-free induced pluripotent stem cells express one or more than one marker for a mature cell type selected from the group consisting of cardiomyocytes, hepatocytes and mesenchymal stem cells.

According to another embodiment of the present invention, there is provided integration-free induced pluripotent stem cell colonies formed by the integration-free induced pluripotent stem cells generated by a method according to the present invention. In one embodiment, the integration-free induced pluripotent stem cell colonies express one or more than one marker for a mature cell type selected from the group consisting of cardiomyocytes, hepatocytes and mesenchymal stem cells.

According to another embodiment of the present invention, there is provided a method of treating a patient having a condition or disease. The method comprises: a) identifying a patient with a condition or disease suitable for treatment by the present method; and b) administering integration-free induced pluripotent stem cells according to the present invention or generated by a method according to the present invention. In one embodiment, the patient is a human. In another embodiment, the condition or disease is selected from the group consisting of an autoimmune disease, cancer, cardiovascular disease, a connective tissue disease, an injury, and a neurodegenerative disease. In another embodiment, identifying the patient comprises diagnosing the patient with one or more than one condition or disease suitable for treatment by the method. In one embodiment, diagnosing the patient comprises performing one or more than one of action selected from the group consisting of performing a physical examination, performing a non-invasive imaging examination, and identifying one or more than one marker for a condition or disease in the blood or other body fluid of the patient. In another embodiment, identifying the patient comprises consulting patient records to determine if the patient has a condition or disease suitable for treatment by the method.

DRAWINGS

These and other features, aspects and advantages of the present invention will become better understood with regard to the following description, appended claims, and accompanying drawings where:

FIG. 1 is a schematic depiction of the self-inactivating (SIN) lentiviral vector backbones for expression of OCT4 (O), SOX2 (S) and OCT4 and SOX2 (OS), where Δ indicates the SIN design with partially deleted U3 of the 3' long terminal repeat, cPPT is a central polypurine tract, Wpre is a post-transcriptional regulatory element, RRE is a rev-responsive element, ψ is a packaging signal, and SFFV is the spleen focus-forming virus U3 promoter;

FIG. 2 is schematic depiction of the self-inactivating (SIN) lentiviral vector backbones for expression of GFP, where Δ indicates the SIN design with partially deleted U3 of the 3' long terminal repeat, cPPT is a central polypurine tract, Wpre is a post-transcriptional regulatory element, RRE is a rev-responsive element, ψ is a packaging signal, SFFV is the spleen focus-forming virus U3 promoter, EF1 is the Elongation factor-1 alpha promoter and PGK is the phosphoglycerokinase promoter;

Figure 5:
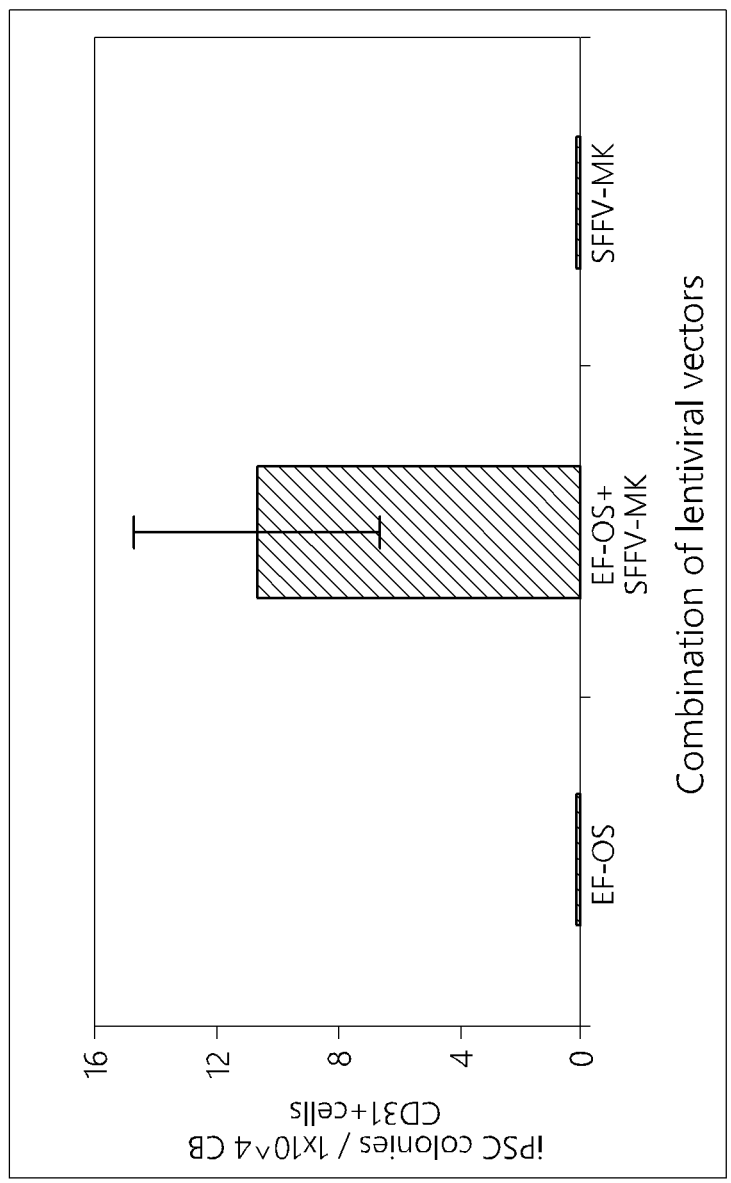
Figure 6:
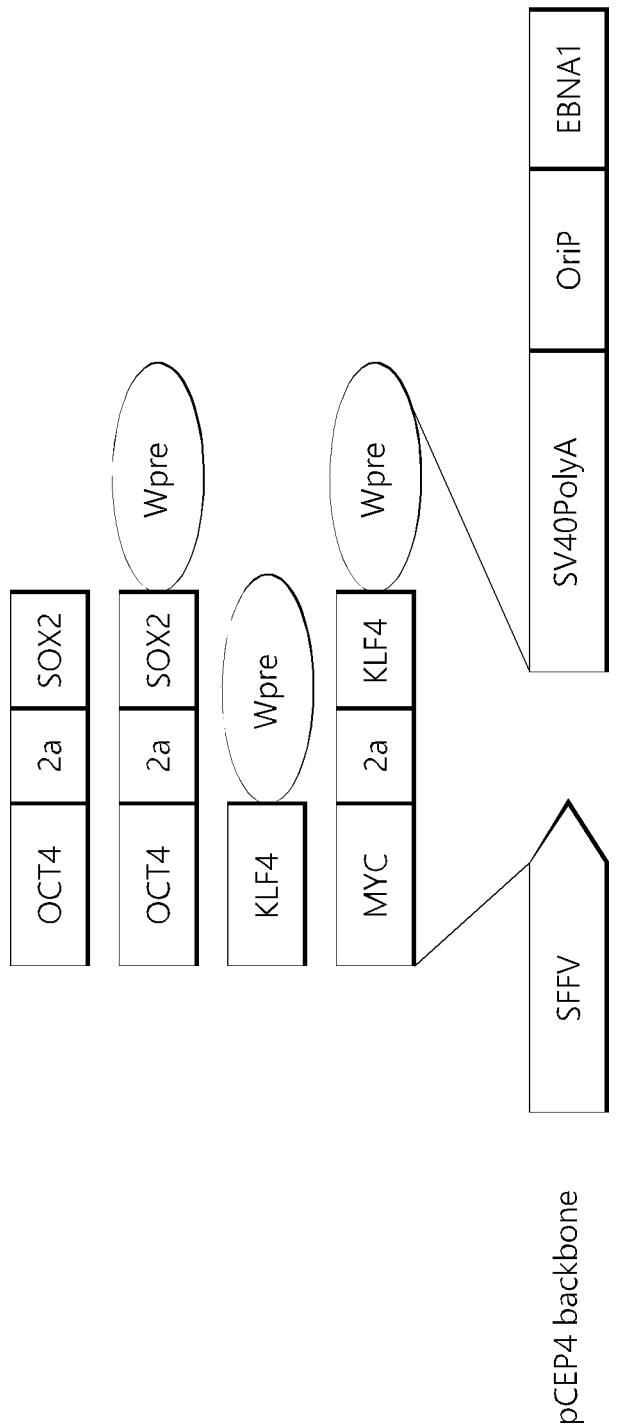
Figure 7:
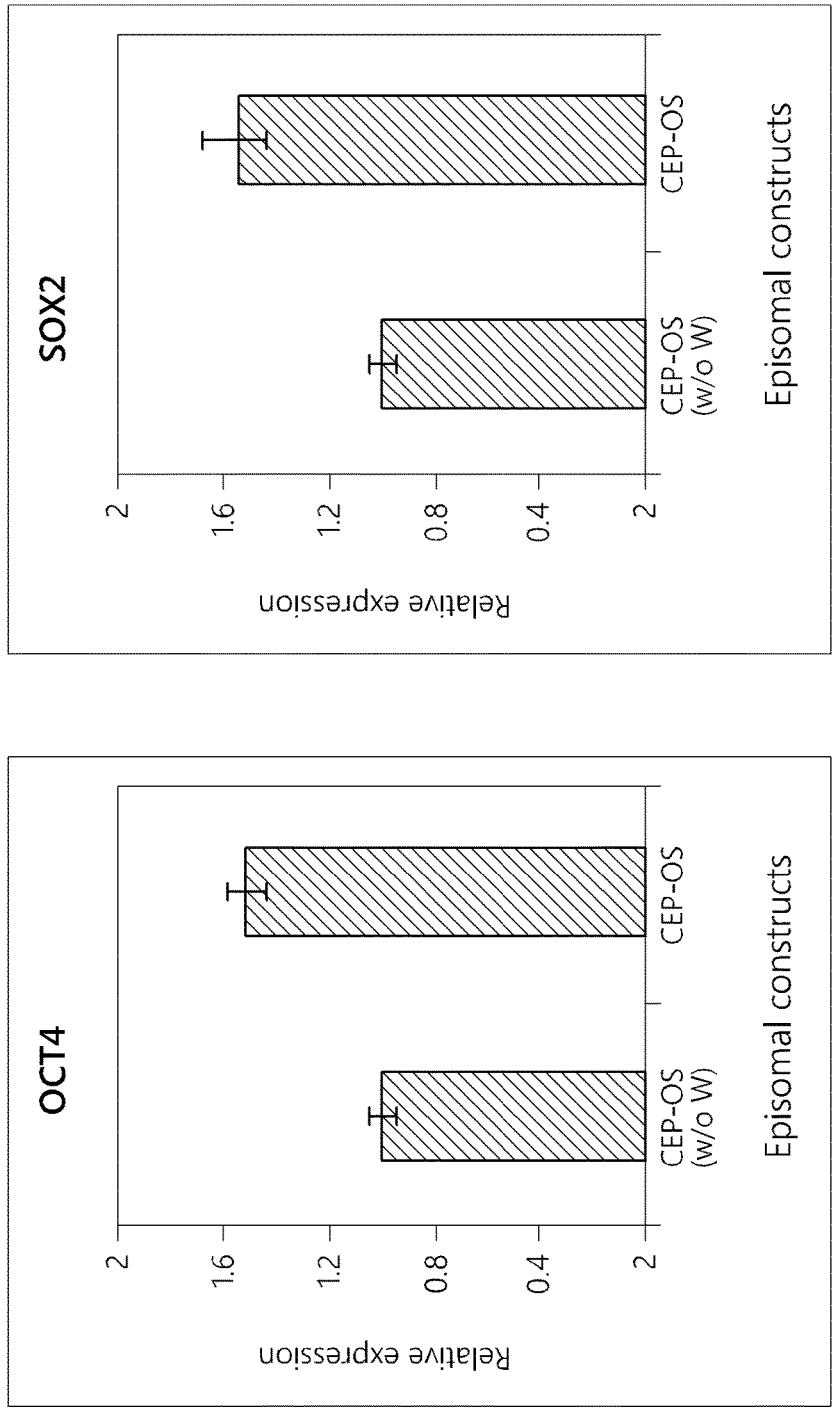
Figure 8:
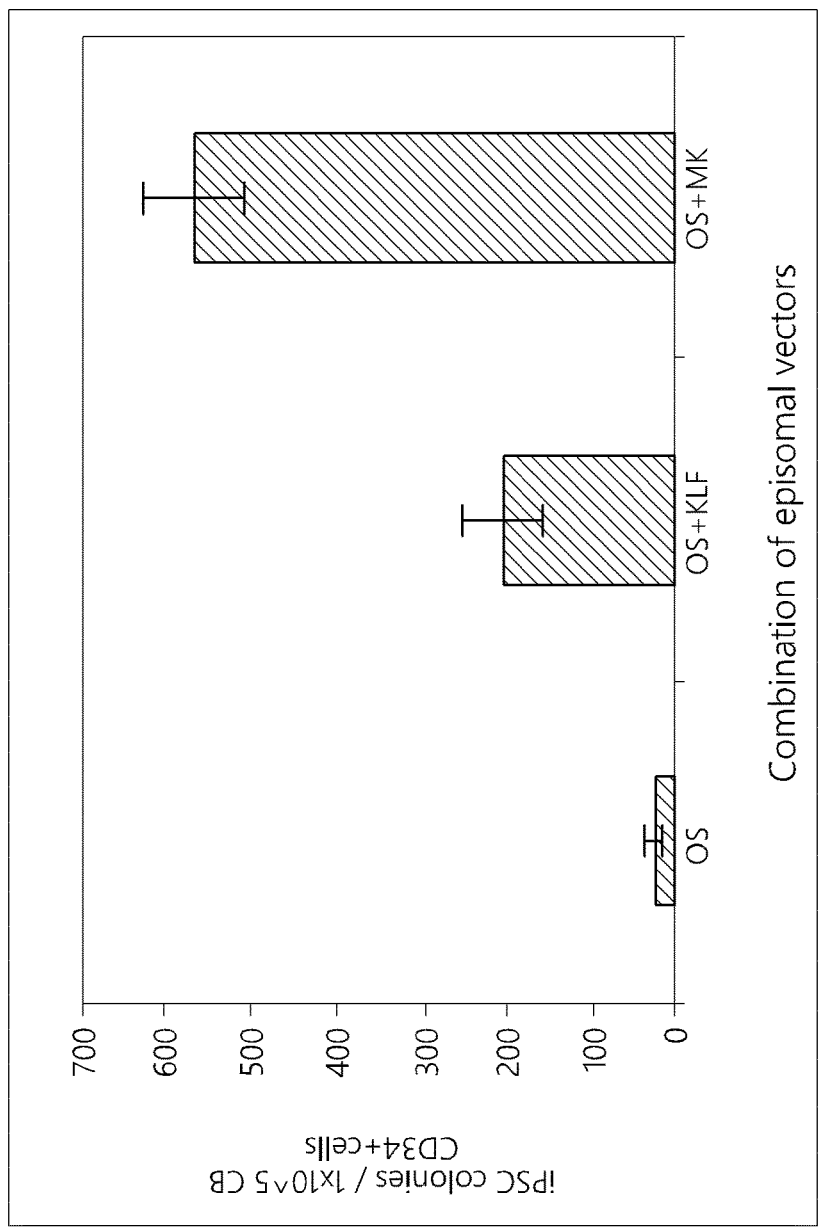
Figure 10:
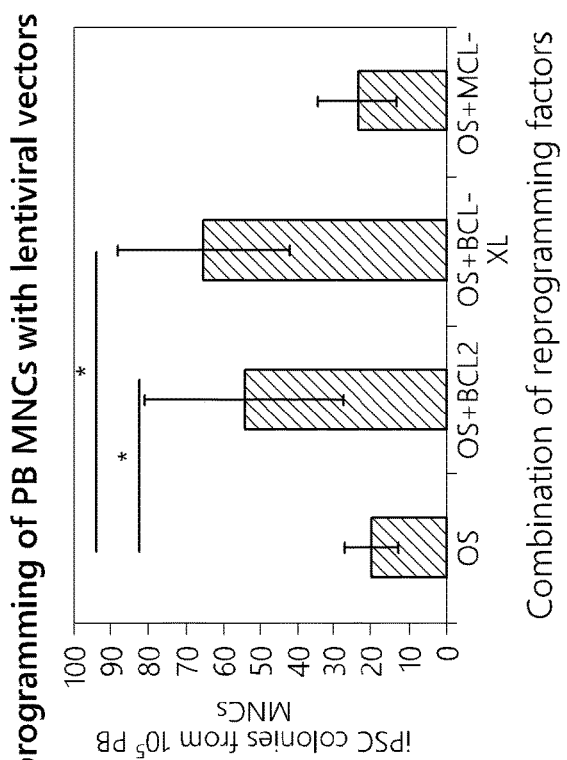
Figure 9:
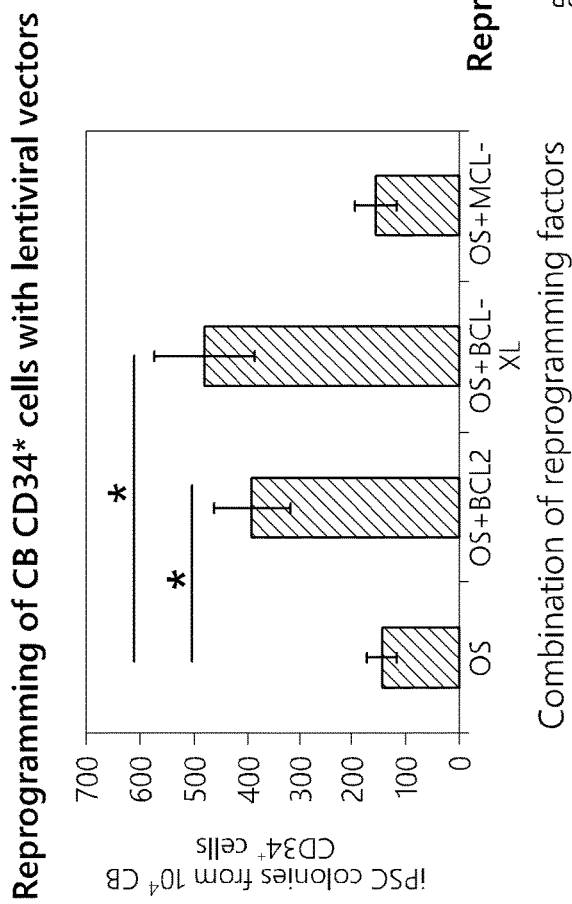
Figure 11B:
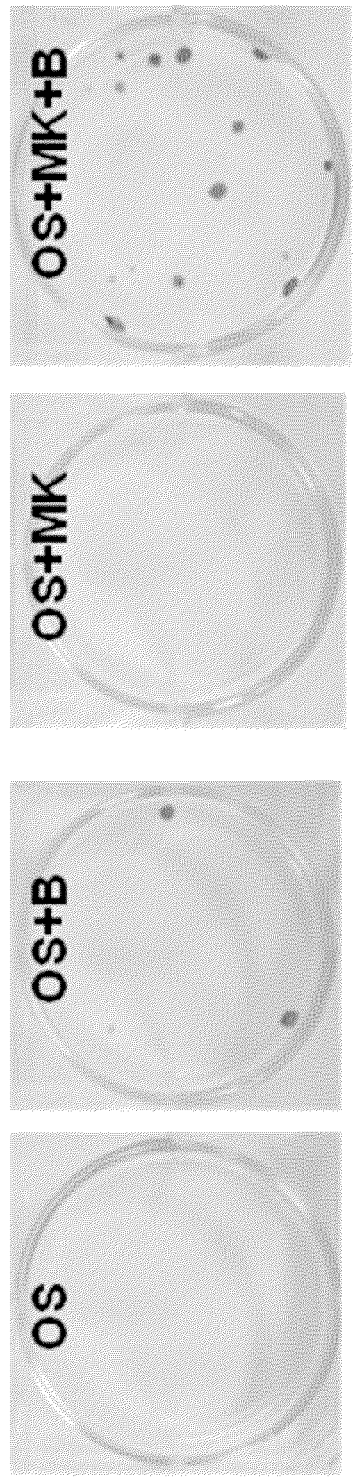
Figure 12A:
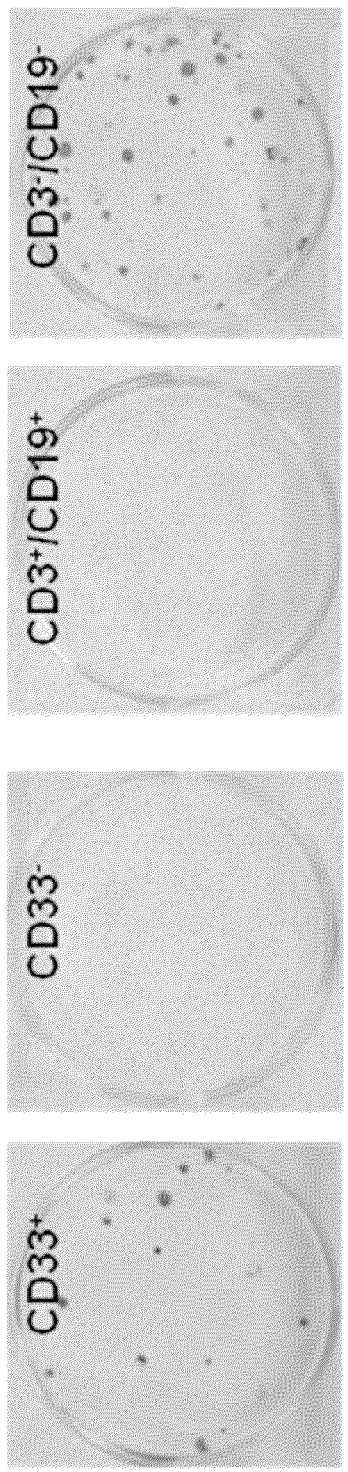
Figure 13:
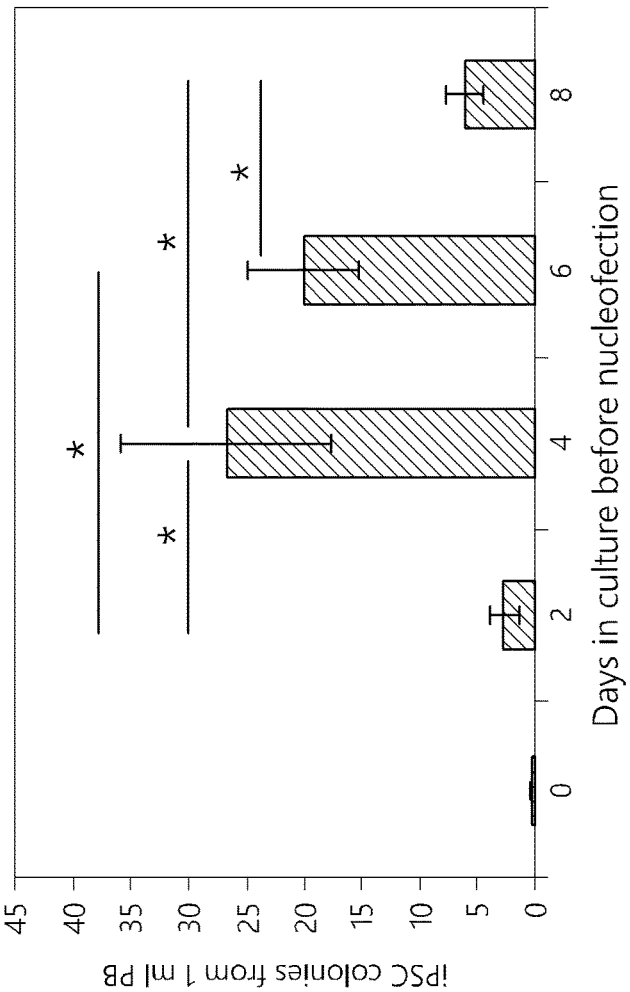
Figure 12B:
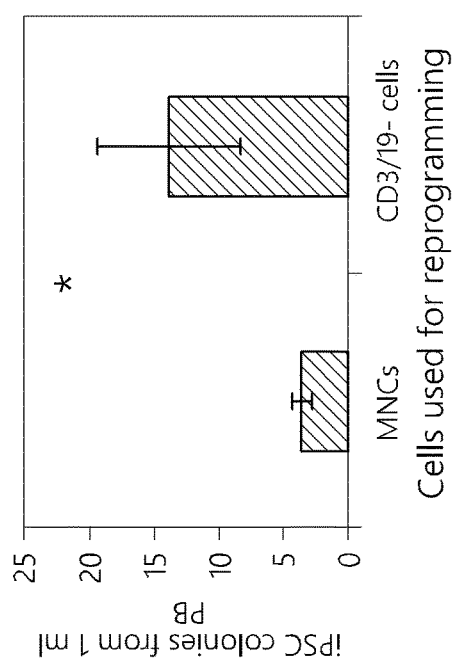
Figure 14B:
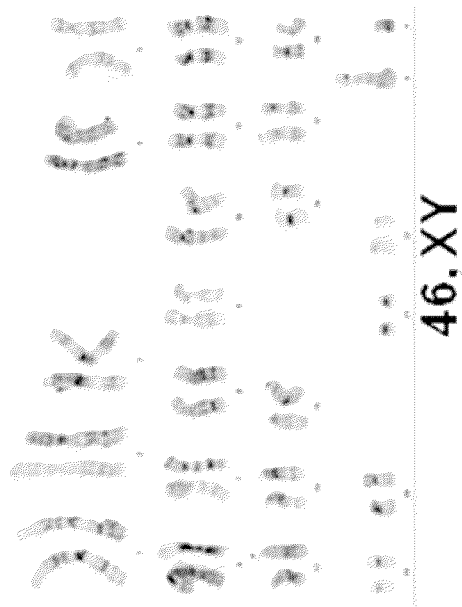
Figure 14A:
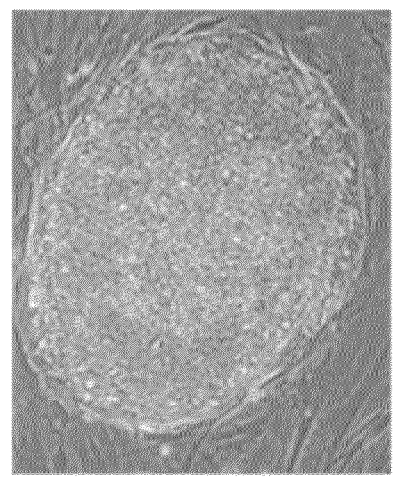
Figure 14C:
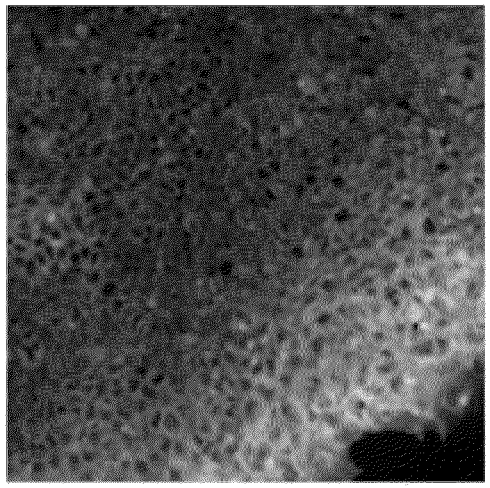
Figure 14C:
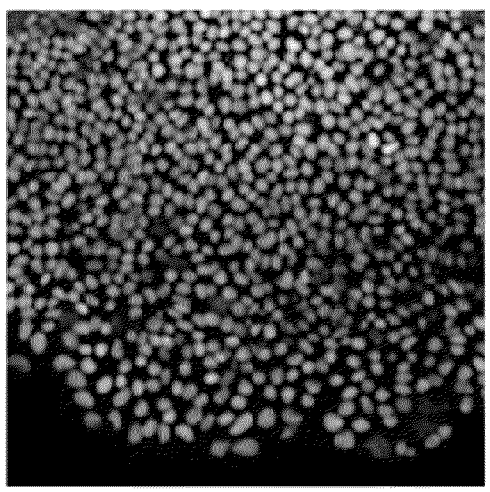
Figure 14C:
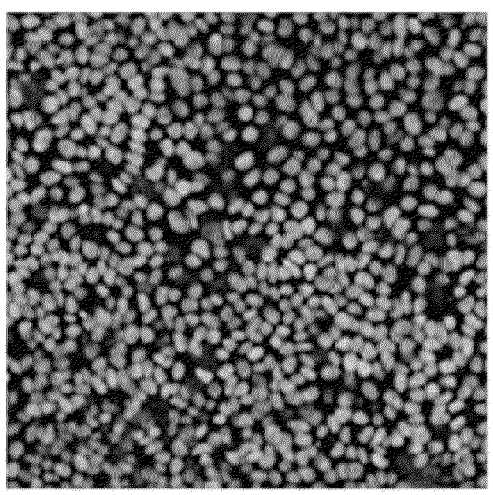
Figure 14D:
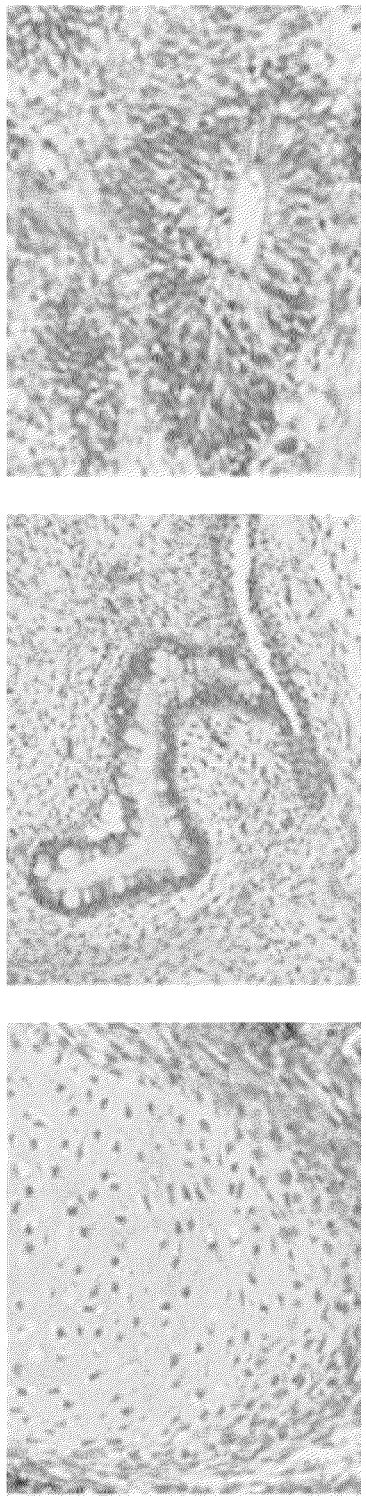
Figure 14E:
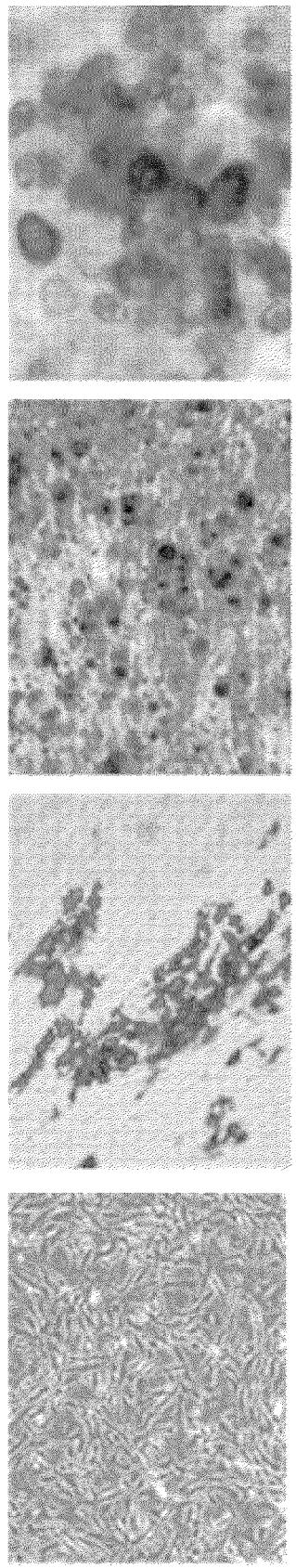
Figure 14F:
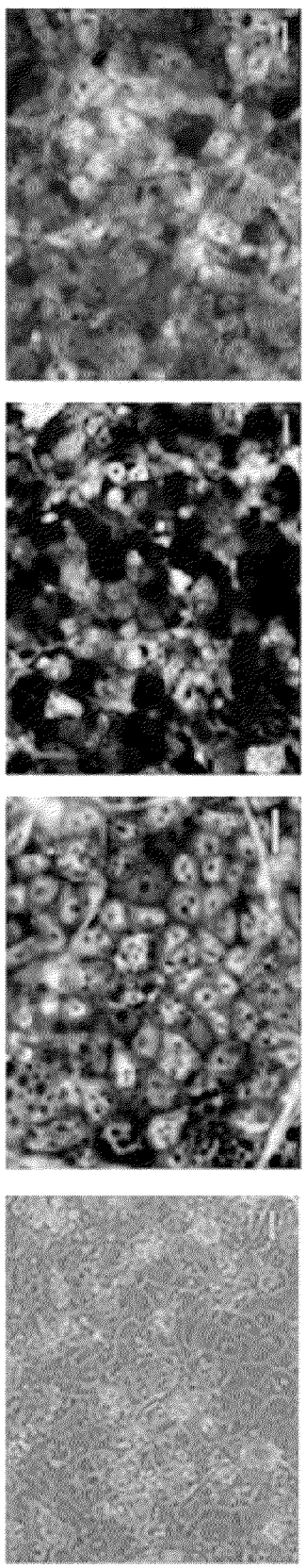
Figure 14G:
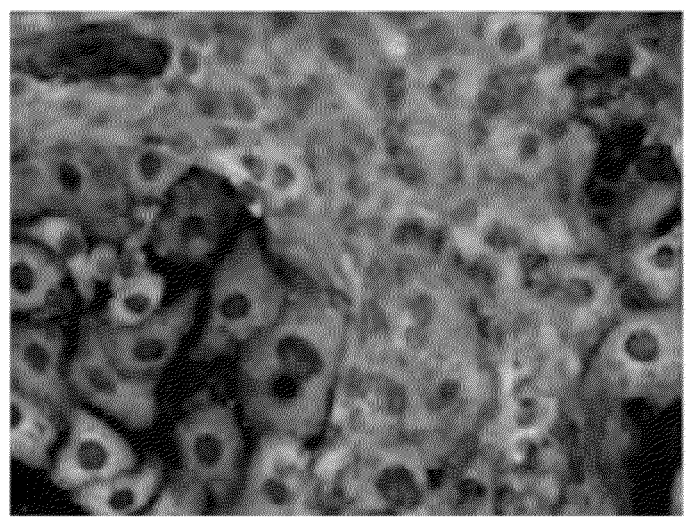

FIG. 5 is a graph of the number of induced pluripotent stem cell colonies generated from $1 \times 10^4$ cord blood CD34+ cells that were transduced only with the vector mediating overexpression of both OCT4 and SOX2 driven by the EF1 promoter (left), transduced with both the vector mediating overexpression of both OCT4 and SOX2 driven by the EF1 promoter and the vector mediating overexpression of MYC driven the SFFV promoter (center), and transduced only with the vector mediating overexpression of MYC driven the SFFV promoter (right);

FIG. 6 is a schematic depiction of an episomal mammalian expression vector backbone (bottom) for (from upper to lower, respectively) co-expression of OCT4 and SOX2 (OS) without Wpre (pCEP-OS (w/o W)), co-expression of OCT4 and SOX2 (OS) with Wpre (pCEP-OS), expression of KLF4 (K) (pCEP-K), and expression of MYC (MK) (pCEP-MK); where 2a is a self-cleavage site derived from equine rhinitis A virus, Wpre is a post-transcriptional regulatory element, SV40PolyA is a polyadenylation signal from SV40 virus, OriP is an EBV origin of replication, and EBNA1 is Epstein-Barr nuclear antigen 1;

FIG. 7 are graphs of the relative expression of OCT4 (left) and SOX2 (right) for cells transfected with pCEP-OS (w/o Wpre) (left bar) and pCEP-OS (with Wpre) (right bar);

FIG. 8 is a graph of the number of induced pluripotent stem cells generated from $1 \times 10^5$ cord blood CD34+ cells transfected with the pCEP-OS episomal vector (OS) (left-most bar), with the pCEP-OS episomal vector and the pCEP-K episomal vector (OS+K) (center bar), or with the pCEP-OS episomal vector and the pCEP-MK episomal vector (OS+MK) (right-most bar);

FIG. 9 is graph of the number of induced pluripotent stem colonies generated from $1 \times 10^4$ cord blood CD34+ cells when reprogrammed by using balanced expression of OCT4 and SOX2 (OS) (left-most bar), OS+BCL2 (center left bar), OS+BCL-XL (center right bar), and OS+MCL (right-most bar);

FIG. 10 is a graph of the number of induced pluripotent stem colonies generated from $1 \times 10^5$ peripheral blood mononuclear cells when reprogrammed by using balanced expression of OCT4 and SOX2 (OS) (left-most), OS+BCL2 (center left), OS+BCL-XL (center right), and OS+MCL (right-most);

FIGS. 11A-11C are, respectively, a schematic depiction of an episomal mammalian expression vector backbone (bottom) for (from upper to lower, respectively) co-expression of OCT4 and SOX2 (pCEP-OS), expression of KLF4 (pCEP-K), expression of BCL-XL (pCEP-B), co-expression of BCL-XL and KLF4 (pCEP-BK), co-expression of OCT4, SOX2, BCL-XL and KLF4 (pCEP-OSBK), and co-expression of MYC and KLF4 (pCEP-MK), where 2a is a self-cleavage site derived from equine rhinitis A virus, SFFV is a spleen focus-forming virus promoter, Wpre is a post-transcriptional regulatory element, SV40PolyA is a polyadenylation signal from SV40 virus, OriP is an EBV origin of replication, and EBNA1 is Epstein-Barr nuclear antigen 1 (FIG. 11A); photographs of alkaline phosphatase staining of induced pluripotent stem cell colonies at four weeks after nucleofection of adult peripheral blood mononuclear cells with episomal vectors expressing OCT4 and SOX2 (OS) (left-most); OCT4, SOX2 (OS) and BCL-XL (OS+B) (center left); OCT4, SOX2, MYC and KLF4 (OS+MK) (center right), and OCT4, SOX2, MYC, KLF4 and BCL-XL (OS+MK+B) (right most) (FIG. 11B); and a graph of the number of induced pluripotent stem colonies generated from 1 ml of adult peripheral blood mononuclear cells nucleofected with the episomal vectors expressing reprogramming factors OCT4 and SOX2 (OS) without BCL-XL/with BCL-XL (left-most two bars); and OCT4, SOX2 and KLF4 (OS+K) without BCL-XL/with BCL-XL (center two bars); and OCT4, SOX2, MYC and KLF4 (OS+MK) without BCL-XL/with BCL-XL (right-most two bars) (FIG. 11C);

FIGS. 12A-12B are, respectively, photographs of alkaline phosphatase staining of induced pluripotent stem cell colonies at four weeks after nucleofection of fractionated adult peripheral blood mononuclear cells with episomal vectors expressing reprogramming factors OCT4, SOX2, MYC, KLF4 and BCL-XL (OS+MK+B), where the fractionated adult peripheral blood mononuclear cells expressed the myeloid lineage marker CD33 (CD33+, left-most), did not express the myeloid lineage marker CD33 (CD33−, center left), expressed the T cell marker CD3 or the B cell marker CD19 (CD3+/CD19+, center right), and did not express the T cell marker CD3 or the B cell marker CD19 (CD3−/CD19−, right-most) (FIG. 12A); and a graph of the number of induced pluripotent stem colonies generated from 1 ml of adult whole peripheral blood mononuclear cells nucleofected with the episomal vectors expressing OCT4, SOX2, MYC, KLF4 and BCL-XL (left bar), and generated from 1 ml of adult peripheral blood mononuclear cells that were T cell/B cell lymphocyte depleted (CD3−/CD19−) nucleofected with the episomal vectors expressing OCT4, SOX2, MYC, KLF4 and BCL-XL (right bar) (FIG. 12B);

FIG. 13 is a graph of the number of induced pluripotent stem cell colonies generated from 1 ml of adult peripheral blood mononuclear cells that were depleted of cells that expressed the T cell marker CD3 or the B cell marker CD19 (CD3−/CD19−), and were then nucleofected with the episomal vectors expressing OCT4, SOX2, MYC, KLF4 and BCL-XL versus the number of days in culture before nucleofection; and FIGS. 14A-14G are, respectively, a photograph of a representative induced pluripotent stem cell colony (FIG. 14A); a photograph of a representative karyogram of an induced pluripotent stem cell clone (FIG. 14B); representative images captured using a Zeiss LSM 710 confocal microscope with a 20× objective of induced pluripotent stem cells immunostained to show expression of pluripotency markers OCT4 (left), SOX2 (center), and NANOG and SSEA4 (right) by representative induced pluripotent stem cell colonies (FIG. 14C); representative images captured using an Olympus microscope with a 20× objective of cell layer derivatives in hematoxylin and eosin (H & E) staining formed by teratomas in immunodeficient mice produced by representative induced pluripotent stem cell colonies, where the teratoma cell layers included all three embryonic germ layers, cartilage (mesoderm, left), glands (endoderm, center) and neurotubules (ectoderm, right) (FIG. 14D); photographs of representative induced pluripotent stem cell colonies showing differentiation into mesenchymal stem cells (leftmost), stained with Oil Red O stains to show the oil droplets of adipocytes (center left), stained with Alizarin Red to show bone nodules formed by osteoblasts (center right), and stained with Alcian Blue to show acid mucopolysaccharides synthesized and secreted by chondrocytes (right-most) (FIG. 14E); photographs of representative induced pluripotent stem cell colonies showing differentiation into hepatocytes (left-most), and stained with monoclonal antibody against alpha-fetoprotein (AFP) to show expression of alpha-fetoprotein (center left), stained with goat anti-albumin to show expression of albumin (ALB), and stained with goat anti-alpha 1-antitrypsin to show expression of alpha 1-antitrypsin ($\alpha$1-AT) (FIG. 14F); and a photograph of representative induced pluripotent stem cell colonies showing expression of Troponin I marker showing differentiation into cardiomyocytes where the cell nuclei are counterstained with 4',6-diamidino-2-phenylindole (FIG. 14G).

DESCRIPTION

According to one embodiment of the present invention, there is provided a vector for generating integration/transgene-free induced pluripotent stem cells from target cells, where the target cells are hematopoietic stem cells or somatic cells. In one embodiment, the vector is a viral vector. In another embodiment, the vector is an episomal vector. The vector comprises a plurality of transcription and reprogramming factor genes. In one embodiment, the vector comprises between two, three or four transcription and reprogramming factor genes. In one embodiment, the vector further comprises one or more than one anti-apoptotic factor. In one embodiment, the vector further comprises a promoter. In one embodiment, the vector further comprises a post-transcriptional regulatory element. According to another embodiment of the present invention, there is provided a method for generating integration/transgene-free induced pluripotent stem cells. The method comprises providing one or more than one vector according to the present invention and transducing or transfecting target cells with the one or more than one vector. In a preferred embodiment, the target cells are hematopoietic stem cells. In another preferred embodiment, the target cells are peripheral blood cells that have been enriched for one or more than one cell type selected from the group consisting of CD33+ cells, CD34+ cells and CD133+ cells, or depleted of cells that express T cell marker CD3 or B cell maker CD19. According to another embodiment of the present invention, there are provided integration/transgene-free induced pluripotent stem cells generated by the method. According to another embodiment of the present invention, there is provided a method of treating a patient having a condition or disease. The method comprises administering integration/transgene-free induced pluripotent stem cells according to the present invention or integration/transgene-free induced pluripotent stem cells generated by a method according to the present invention.

Among the various aspects of the present invention are: 1) selecting a vector based on an oriP/EBNA1-based plasmid backbone episomal vector (EV), 2) incorporating exactly two, exactly three or exactly four transcription and reprogramming factor genes in the vector rather than the five or more transcription and reprogramming factor genes currently being used, and in particular incorporating the combination of oct4 gene and sox2 gene alone, or the combination of oct4 gene, sox2 gene and klf4 gene alone, with or without a myc gene, but without other transcription and reprogramming factor genes, 3) incorporating an anti-apoptotic factor gene, such as a gene expressing BCL-XL or BCL2 into the vector, 4) incorporating a strong spleen focus-forming virus (SFFV) promoter in the vector, 5) incorporating a post-transcriptional regulatory element such as Wpre, 6) selecting peripheral blood cells that have been enriched for one or more than one cell type selected from the group consisting of CD33+ cells, CD34+ cells and CD133+ cells, or depleted of cells that express T cell marker CD3 or B cell maker CD19 as the target cells for reprogramming; or depleting the target cells of cells that express T cell marker CD3 or B cell maker CD19 as the target cells for reprogramming, and 7) culturing the target cells before transduction or transfection in a cell culture for a duration of between three days and six days, and preferably about four days, which is optimal for generation of integration/transgene-free induced pluripotent stem cells. Using these techniques, integration/transgene-free induced pluripotent stem cells can be generated from adult peripheral blood in quantities of between twenty and thirty integration-free induced pluripotent stem cells/colonies from 1 ml peripheral blood, an efficiency that is substantially higher (between ten to one thousand times higher) than previously reported. Further, the integration/transgene-free induced pluripotent stem cells generated according to the present invention were shown to differentiate into cardiomyocytes, hepatocytes and mesenchymal stem cells, among other cell types, all of which appeared to be morphologically, phenotypically and functionally normal. The integration/transgene-free induced pluripotent stem cells according to the present invention and generated by a method according to the present invention have potential applications in allogeneic cell therapy for regenerative medicine, disease modeling, and induced pluripotent stem cell banking, among other uses. The vectors, methods and cells will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed are not intended to be limiting nor are they intended to indicate that each step is essential to the method or that each step must occur in the order disclosed.

As used in this disclosure, except where the context requires otherwise, "integration-free induced pluripotent stem cells" is synonymous with "integration/transgene-free induced pluripotent stem cells" and is understood to mean that after eight passages, the average copy number of residual vector is less than 0.01 copies per genome.

As presented in this disclosure, except where otherwise specified, data are presented as mean±standard error of the mean (SEM), two-tailed Student t test was performed, and P values of <0.05 were considered statistically significant.

According to one embodiment of the present invention, there is provided a vector for generating induced pluripotent stem cells from target cells. In one embodiment, the vector is a plasmid. In a preferred embodiment, the vector is a non-integrating plasmid. In one embodiment, the vector is a non-plasmid. In one embodiment, the vector is a non-integrating vector. In one embodiment, the vector is a viral vector. In one embodiment, the vector is a non-integrating viral vector. In one embodiment, the vector is a self-inactivating (SIN) vector. In one embodiment, the vector is a lentivirus. In one embodiment, the vector is an episomal vector. In a preferred embodiment, the vector is an oriP/EBNA1-based episomal vector. In one embodiment, the vector is an oriP/EBNA1-based plasmid backbone episomal vector (EV).

The vector comprises a plurality of transcription and reprogramming factor genes. In one embodiment, the plurality of transcription and reprogramming factor genes is exactly two transcription and reprogramming factor genes. In another embodiment, the plurality of transcription and reprogramming factor genes is exactly three transcription and reprogramming factor genes. In another embodiment, the plurality of transcription and reprogramming factor genes is exactly four transcription and reprogramming factor genes. In another embodiment, the plurality of transcription and reprogramming factor genes is exactly five transcription and reprogramming factor genes.

In one embodiment, the transcription and reprogramming factor genes are selected from the group consisting of one or more than one Yamanaka factor gene and one or more than one Thomson/Yu factor gene, and a combination of the preceding. In one embodiment, the transcription and reprogramming factor genes are selected from the group consisting of a) octamer-binding transcription factor 4 gene (Octamer-4 gene; oct4 gene, encoding Octomer-4; OCT4) (also known as pou5f1, encoding POU5F1), b) (sex determining region Y)-box 1 gene (sox1 gene) (encoding SOX1), (sex determining region Y)-box 2 gene (sox2 gene) (encoding SOX2), c) (sex determining region Y)-box 3 gene (sox3 gene) (encoding SOX3), d) (sex determining region Y)-box 15 gene (sox15 gene) (encoding SOX15), e) (sex determining region Y)-box 18 gene (sox18 gene) (encoding SOX18), f) Krueppel-like factor 4 gene (klf4 gene) (encoding Krueppel-like factor 4 protein; KLF4 protein), g) myelocytomatosis gene (myc gene; MYC) (encoding Myc protein), h) nanog (encoding NANOG protein) and i) lin28 (encoding Lin-28 homolog A protein).

In one embodiment, the transcription and reprogramming factor genes are exactly two genes, oct4 gene and sox2 gene without other transcription and reprogramming factor genes. In another embodiment, the transcription and reprogramming factor genes are exactly three genes, oct4 gene, sox2 gene and klf4 gene without other transcription and reprogramming factor genes. In another embodiment, the transcription and reprogramming factor genes are exactly four genes, oct4 gene, sox2 gene, klf4 gene and myc gene without other transcription and reprogramming factor genes.

In one embodiment, the vector further comprises one or more than one gene coding for an inhibitor, siRNA, or shRNA construct of a pro-apoptotic factor. In a preferred embodiment, the pro-apoptotic factor is a BAX subfamily pro-apoptotic factor. In a particularly preferred embodiment, the pro-apoptotic factor is a BAX subfamily pro-apoptotic factor selected from the group consisting of BAK, BAX and BOK. In another preferred embodiment, the pro-apoptotic factor is a BH3 subfamily pro-apoptotic factor. In a particularly preferred embodiment, the pro-apoptotic factor a BH3 subfamily pro-apoptotic factor selected from the group consisting of BAD, BID, BIK, BIML, BLK, BNIP3 and HRK.

In a preferred embodiment, the vector further comprises one or more than one anti-apoptotic factor gene encoding one or more than one anti-apoptotic factor. In one embodiment, the one or more than one anti-apoptotic factor is a BCL-2 family anti-apoptotic factor. In another preferred embodiment, the one or more than one anti-apoptotic factor is selected from the group consisting of A1, BCL2, BCL-W, BCL-XL and MCL1. In a particularly preferred embodiment, the anti-apoptotic factor is BCL-XL (B-cell lymphoma-extra large) or BCL2.

In one embodiment, at least two of the plurality of transcription and reprogramming factor genes are linked with a cleavage sequence. In a preferred embodiment, the cleavage sequence is a 2a self-cleavage peptide sequence. In a particularly preferred embodiment, the 2a self-cleavage peptide sequence is selected from the group consisting of equine rhinitis A virus (E2A), foot-and-mouth disease virus (F2A), porcine teschovirus-1 (P2A) and Thosea asigna virus (T2A).

In one embodiment, the vector further comprises a promoter suitable for promoting transcription of at least one of the plurality of transcription and reprogramming factor genes. In one embodiment, the promoter is selected from the group consisting of CAG promoter, CMV promoter, EF1a promoter and ubiquitin promoter. In a preferred embodiment, the promoter is strong spleen focus forming virus (SFFV) promoter (strong spleen focus forming virus (SFFV) long terminal repeat (LTR) promoter; spleen focus-forming virus U3 promoter).

In one embodiment, the vector further comprises a post-transcriptional regulatory element. In a preferred embodiment, the post-transcriptional regulatory element is Wpre. In a preferred embodiment, the post-transcriptional regulatory element is Wpre at the 3' end of the transgene and in front of a PolyA signal.

In one embodiment, the vector is an episomal vector comprising a strong spleen focus-forming virus promoter, a post-transcriptional regulatory element Wpre, and exactly two transcription and reprogramming factor genes, oct4 and sox2. In one embodiment, vector is an episomal vector comprising a strong spleen focus-forming virus promoter, a post-transcriptional regulatory element Wpre, an anti-apoptotic factor gene bcl-xl, and exactly two transcription and reprogramming factor genes, oct4 and sox2. In another embodiment, the vector is an episomal vector comprising a strong spleen focus-forming virus promoter, a post-transcriptional regulatory element Wpre, and exactly three transcription and reprogramming factor genes, oct4, sox2 and klf4. In another embodiment, the vector is an episomal vector comprising a strong spleen focus-forming virus promoter, a post-transcriptional regulatory element Wpre, an anti-apoptotic factor gene bcl-xl, and exactly three transcription and reprogramming factor genes, oct4, sox2 and klf4. In another embodiment, the vector is an episomal vector comprising a strong spleen focus-forming virus promoter, a post-transcriptional regulatory element Wpre, and exactly four transcription and reprogramming factor genes, oct4, sox2, klf4 and myc. In another embodiment, the vector is an episomal vector comprising a strong spleen focus-forming virus promoter, a post-transcriptional regulatory element Wpre, an anti-apoptotic factor gene bcl-xl, and exactly four transcription and reprogramming factor genes, oct4, sox2, klf4 and myc.

According to another embodiment of the present invention, there is provided a method for generating integration-free induced pluripotent stem cells. The method comprises providing target cells, providing one or more than one vector according to the present invention, and transducing or transfecting the target cells with the one or more than one vector. In one embodiment, the one or more than one vector is one vector. In another embodiment, the one or more than one vector is a plurality of vectors. In another embodiment, the one or more than one is two vectors. In another embodiment, one or more than one vector is three vectors.

In one embodiment, one of the one or more than one vector is an episomal vector comprising a strong spleen focus-forming virus promoter, a post-transcriptional regulatory element Wpre, and exactly two transcription and reprogramming factor genes, oct4 and sox2. In one embodiment, the vector is an episomal vector comprising a strong spleen focus-forming virus promoter, a post-transcriptional regulatory element Wpre, an anti-apoptotic factor gene bcl2 or bcl-xl, and exactly two transcription and reprogramming factor genes, oct4 and sox2. In another embodiment, one of the one or more than one vector is an episomal vector comprising a strong spleen focus-forming virus promoter, a post-transcriptional regulatory element Wpre, and exactly three transcription and reprogramming factor genes, oct4, sox2 and klf4. In another embodiment, one of the one or more than one vector is an episomal vector comprising a strong spleen focus-forming virus promoter, a post-transcriptional regulatory element Wpre, an anti-apoptotic factor gene bcl2 or bcl-xl, and exactly three transcription and reprogramming factor genes, oct4, sox2 and klf4. In another embodiment, one of the one or more than one vector is an episomal vector comprising a strong spleen focus-forming virus promoter, a post-transcriptional regulatory element Wpre, and exactly four transcription and reprogramming factor genes, oct4, sox2, klf4 and myc. In another embodiment, one of the one or more than one vector is an episomal vector comprising a strong spleen focus-forming virus promoter, a post-transcriptional regulatory element Wpre, an anti-apoptotic factor gene bcl2 or bcl-xl, and exactly four transcription and reprogramming factor genes, oct4, sox2, klf4 and myc.

In one embodiment, the one or more than one vector is a first vector and a second vector. By way of example only, in one embodiment, the first vector is an episomal vector comprising a strong spleen focus-forming virus promoter, a post-transcriptional regulatory element Wpre, and exactly two transcription and reprogramming factor genes, oct4 and sox2, and the second vector is an episomal vector comprising a strong spleen focus-forming virus promoter, a post-transcriptional regulatory element Wpre, and exactly two transcription and reprogramming factor genes, klf4 and myc. The first vector and the second vector can, however, be any suitable vectors for generating the integration-free induced pluripotent stem cells, as will be understood by those with skill in the art with respect to this disclosure. Similarly, where the one or more than one vector is three vectors, four vectors or five vectors, each of the vectors can be any suitable vector for generating the integration-free induced pluripotent stem cells, as will be understood by those with skill in the art with respect to this disclosure.

In a preferred embodiment, the one or more than one vector is a first vector and a second vector, and transducing or transfecting the target cells comprises transducing or transfecting the target cells with a first amount of the first vector and a second amount of a second vector, where the first amount is equal to the second amount. In another preferred embodiment, the one or more than one vector is a first vector and a second vector, and transducing or transfecting the target cells comprises transducing or transfecting the target cells with a first amount of the first vector and a second amount of a second vector, where the first amount is half of the second amount. The first amount of the first vector and the second amount of a second vector can, however, be in any suitable ratio for generating the integration-free induced pluripotent stem cells, as will be understood by those with skill in the art with respect to this disclosure.

In one embodiment, the one or more than one vector is an episomal vector comprising a strong spleen focus-forming virus promoter, a post-transcriptional regulatory element Wpre, and exactly two transcription and reprogramming factor genes, oct4 and sox2, and the method further comprises transducing or transfecting the target cells with an additional episomal vector comprising a strong spleen focus-forming virus promoter, a post-transcriptional regulatory element Wpre, an anti-apoptotic factor gene bcl-xl, and exactly one transcription and reprogramming factor gene, klf4. In one embodiment, the one or more than one vector is an episomal vector comprising a strong spleen focus-forming virus promoter, a post-transcriptional regulatory element Wpre, and exactly two transcription and reprogramming factor genes, oct4 and sox2, and the method further comprises transducing or transfecting the target cells with a first additional episomal vector comprising a strong spleen focus-forming virus promoter, a post-transcriptional regulatory element Wpre, and exactly one transcription and reprogramming factor gene, klf4, and with a second additional episomal vector comprising a strong spleen focus-forming virus promoter, a post-transcriptional regulatory element Wpre, and an anti-apoptotic factor gene bcl-xl, but without any transcription and reprogramming factor gene. Other combinations of vectors according to the present invention and additional vectors are suitable, as will be understood by those with skill in the art with respect to this disclosure.

In one embodiment, the target cells are hematopoietic stem cells. In another embodiment, the target cells are peripheral blood mononuclear cells. In another embodiment, the target cells are peripheral blood myeloid cells. In another embodiment, the target cells are peripheral blood cells that have been enriched for one or more than one cell type selected from the group consisting of CD33+ cells, CD34+ cells and CD133+ cells. In another embodiment, the target cells are peripheral blood mononuclear cells that have been enriched for CD33+ cells. In a preferred embodiment, the target cells are peripheral blood cells that have been depleted of cells that express T cell marker CD3 or B cell maker CD19.

In one embodiment, the method further comprises harvesting the target cells from a body fluid or tissue. In one embodiment, the body fluid or tissue is selected from the group consisting of bone marrow, cord blood and peripheral blood. In a preferred embodiment, the body fluid or tissue is peripheral blood. In one embodiment, the method further comprises providing cord blood, and further comprises purifying the cord blood to obtain the target cells. In one embodiment, the cord blood is obtained from a cord blood bank. In another embodiment, the method further comprises enhancing or purifying the target cells for cells that express a CD33 marker. In another embodiment, the method further comprises enhancing or purifying the target cells for cells that express a CD34 marker or a CD133 marker. In another embodiment, the method further comprises depleting the target cells of cells that express a T cell marker CD3 or a B cell maker CD19. In another embodiment, the method further comprises enhancing or purifying the target cells for cells that express a CD33 marker, and depleting the target cells of cells that express a T cell marker CD3 or a B cell maker CD19.

Next, the method further comprises culturing the transduced or transfected cells in a cell culture, thereby generating integration-free induced pluripotent stem cells. In one embodiment, the method further comprises purifying integration-free induced pluripotent stem cells from the cell culture after generating the integration-free induced pluripotent stem cells.

In another embodiment, the method further comprises culturing the target cells in a cell culture for a duration of between three days and six days before transducing or transfecting the target cells. In another embodiment, the method further comprises culturing the target cells in a cell culture for a duration of four days before transducing or transfecting the target cells.

In a preferred embodiment, the method comprises incorporating sodium butyrate into the cell culture. In a preferred embodiment, the sodium butyrate is incorporated into the cell culture at a concentration of between 0.1 and 1.0 mM. In a particularly preferred embodiment, the sodium butyrate is incorporated into the cell culture at a concentration of 0.25 mM. In one embodiment, the transduced or transfected cells are cultured in hematopoietic stem cell culture condition such as Iscove's modified Dulbecco's medium (IMDM)/ 10% FBS supplemented with the cytokines Flt3-ligand (FL), granulocyte colony-stimulating factor (G-CSF), stem cell factor (SCF) and thrombopoietin (TPO) each at 100 ng/ml, and Interleukin 3 (IL-3) at 10 ng/ml (ProSpec-Tany Technogene Ltd., East Brunswick, N.J., US). After two days pre-stimulation, $1 \times 10^4$ cells per well are seeded into non-tissue culture, treated twenty-four well plates that were pre-coated with RetroNectin (CH-296; Takara Bio, Inc., Shiga, JP) for lentiviral transduction for four to five hours. A second transduction is conducted twenty-four hours later. One day after transduction, the cells are harvested and transferred to six-well plates, which are pre-seeded with a mitomycin C-inactivated CF-1 mouse embryonic fibroblast (MEF) feeder layer (Applied Stemcell, Inc., Menlo Park, Calif., US). Cells are maintained in the hematopoietic stem cell culture condition for two more days before being replaced with induced pluripotent stem cell media, such as for example Knockout DMEM/F12 medium supplemented with 20% Knockout Serum Replacement (KSR), 1 mM GlutaMAX, 2 mM nonessential amino acids, lx penicillin/ streptomycin (all from Invitrogen, Grand Island, N.Y., US), 0.1 mM β-mercaptoethanol (Sigma-Aldrich Corp., St. Louis, Mo., US), 20 ng/ml FGF2 (ProSpec). In a preferred embodiment, sodium butyrate is added at 0.25 mM from day two to twelve, and cells are cultured under hypoxia by placing culture plates in a Hypoxia Chamber (Stemcell Technologies, inc., Vancouver, BC, CA) that is flushed with mixed air composed of 92% N2/3% O2/5% CO2. Starting from day ten, mouse embryonic fibroblast-conditioned medium is used.

According to another embodiment of the present invention, there are provided integration-free induced pluripotent stem cells generated by the method. In one embodiment, the integration-free induced pluripotent stem cells express one or more than one marker for a mature cell type selected from the group consisting of cardiomyocytes, hepatocytes and mesenchymal stem cells. According to another embodiment of the present invention, there are provided integration-free induced pluripotent stem cell colonies formed by the integration-free induced pluripotent stem cells generated by the method. In one embodiment, the integration-free induced pluripotent stem cell colonies express one or more than one marker for a mature cell type selected from the group consisting of cardiomyocytes, hepatocytes and mesenchymal stem cells.

According to another embodiment of the present invention, there is provided a method of treating a patient having a condition or disease. The method comprises identifying a patient with a condition or disease suitable for treatment by the present method, and administering integration-free induced pluripotent stem cells according to the present invention or generated by a method according to the present invention. In a preferred embodiment, the patient is a human. In one embodiment, the condition or disease is selected from the group consisting of an autoimmune disease, cancer, cardiovascular disease, a connective tissue disease, an injury, and a neurodegenerative disease. In one embodiment, identifying the patient comprises diagnosing the patient with one or more than one condition or disease suitable for treatment by the present method. In one embodiment, diagnosing the patient comprises performing one or more than one of action selected from the group consisting of performing a physical examination, performing a non-invasive imaging examination (such as for example computerized tomography, magnetic resonance imaging and ultrasound), and identifying one or more than one marker for a condition or disease in the blood or other body fluid of the patient. In another embodiment, identifying the patient comprises consulting patient records to determine if the patient has a condition or disease suitable for treatment by the present method.

Example 1

Figure 1:
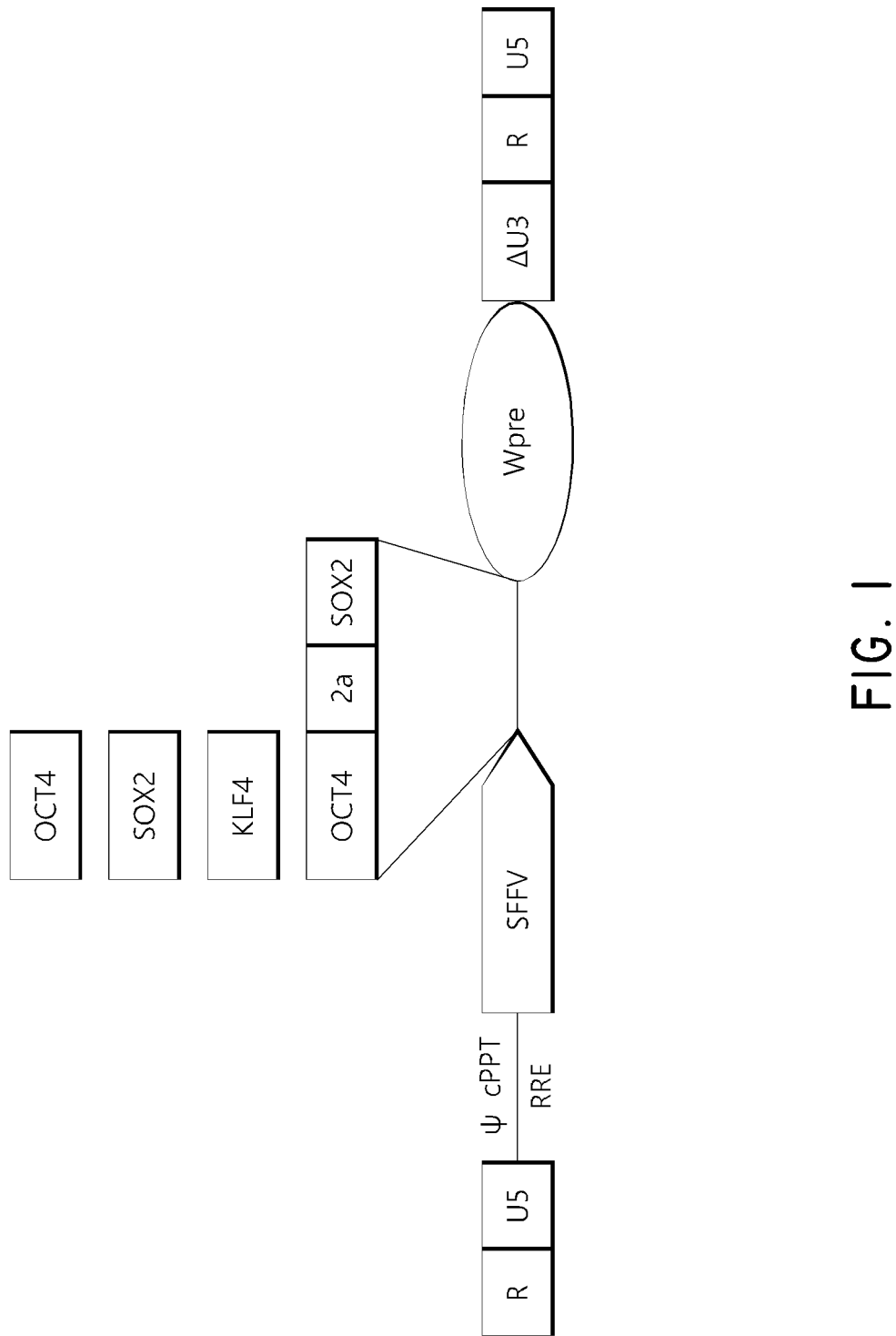

Determination of Whether Co-Expression of Both OCT4 and SOX2 in a Single Vector Driven by a Strong Promoter Generated More Induced Pluripotent Stem Cells than Simultaneous Expression of Both OCT4 and SOX2 by Separate Vectors A determination was made as follows, whether co-expression of both OCT4 and SOX2 in a single vector driven by a strong promoter generated more induced pluripotent stem cells than simultaneous expression of both OCT4 and SOX2 by separate vectors from cord blood CD133+ cells. It has been previously shown that overexpression of OCT4 together with SOX2 using two separate retroviral vectors (O+S) can generate induced pluripotent stem cells from cord blood CD133+ cells. However, the two retroviral vector combination yielded a generation efficiency of between 0.002% and 0.005% which is too low for practical clinical use. To determine if this low efficiency was due to inadequate retroviral vector-mediated overexpression of OCT4 and SOX2, lentiviral vectors mediating overexpression of OCT4 alone (O), overexpression of SOX2 alone (S), and overexpression of both OCT4 and SOX2 in a single vector with a self-cleavage peptide sequence 2a between the OCT4 gene and the SOX2 gene (OS) were produced, where expression in each of the three vectors was driven by spleen focus-forming virus (SFFV) promoter (a strong promoter in primary hematopoietic cells and hematopoietic cell lines). Referring now to FIG. 1, there is shown a schematic depiction of the self-inactivating (SIN) lentiviral vector backbones for expression of OCT4 (O), SOX2 (S) and OCT4 and SOX2 (OS), where Δ indicates the SIN design with partially deleted U3 of the 3' long terminal repeat, cPPT is a central polypurine tract, Wpre is a post-transcriptional regulatory element, RRE is a rev-responsive element, ψ is a packaging signal, and SFFV is the spleen focus-forming virus U3 promoter.

CD34+ cells were purified from cord blood with a CD34+ MicroBead Kit (Miltenyi Biotec, Auburn, Calif., US). The purified CD34+ cells were transduced with either the combination of the lentiviral vector mediating overexpression of OCT4 and the lentiviral vector mediating overexpression of SOX2 (O+S), or were transduced with the single lentiviral vector mediating overexpression of both OCT4 and SOX2 (OS). The transduced cells were cultured on mouse embryonic fibroblasts (MEFs).

Four to five days after seeding the transduced cord blood CD34+ cells onto the mouse embryonic fibroblasts, the O+S cells had formed dozens of small colonies in each well; however, morphologically induced pluripotent stem cells did not appear until approximately twelve days after seeding. The cells that appeared in the first four to five days were analyzed by flow cytometry and many of these cells expressed mesenchymal markers. The O+S cells produced between 300 and 600 total colonies in each well from 10,000 transfected cord blood CD34+ cells eight to ten days after transduction. However, the majority of colonies were morphologically not induced pluripotent stem cells and alkaline phosphatase (ALP) staining showed that only about 20% of the colonies stained like induced pluripotent stem cells.

By contrast, the cells transduced with the single lentiviral vector mediating overexpression of both OCT4 and SOX2 (OS cells) did not produce any colonies at all in the first week after transduction, but produced the first morphologically induced pluripotent stem cells-like colonies eight to ten days after transduction. The OS cells produced between 200 and 250 total colonies in each well, with about 80% of the colonies being morphologically induced pluripotent stem cells. Alkaline phosphatase (ALP) staining showed that about 80% of the colonies stained like induced pluripotent stem cells. Fluorescence-activated cell sorting (FACS) analysis was also performed on both groups of cultures. About 9% of the cells generated from the O+S cells expressed the induced pluripotent stem cells marker TRA-1-60, while about 40% of the cells generated from the OS cells expressed the induced pluripotent stem cells marker TRA-1-60. Therefore, simultaneous expression of both OCT4 and SOX2 by separate vectors driven by a strong promoter is sufficient to generate induced pluripotent stem cells from cord blood cells, while the co-expression of both OCT4 and SOX2 in a single vector driven by the same promoter generated more induced pluripotent stem cells than the separate simultaneous expression, and additionally inhibited the growth of other non-induced pluripotent stem cells.

Example 2

Determination of Whether KLF4 Increased Efficiency of Generation of Induced Pluripotent Stem Cells by Co-Expression of Both OCT4 and SOX2 in a Single Vector Driven by a Strong Promoter Next, a determination was made as follows, whether adding another transcription and reprogramming factor known to generate induced pluripotent stem cells from somatic cells increased efficiency of generation of induced pluripotent stem cells by co-expression of both OCT4 and SOX2 in a single vector driven by a strong promoter. The test transcription and reprogramming factor used was Krueppel-like factor 4 (KLF4, a protein encoded by klf4). A single lentiviral vector mediating simultaneous overexpression of OCT4, SOX2 and KLF4 was produced, and used to transduce CD34+ cells as in Example 1. Expression of KLF4 by the transfected cells was confirmed. Approximately 2% of the CD34+ cells transfected converted into induced pluripotent stem cells, about the same amount as using the lentivirus simultaneously expressing both OCT4 and SOX2 only without the KLF4 in Example 1. Approximately 40% of the cells in the culture expressed the induced pluripotent stem cells marker TRA-1-60, slightly higher than using the lentivirus simultaneously expressing both OCT4 and SOX2 only without the KLF4 in Example 1; however, the difference did not rise to the level of statistical significance. Therefore, addition of another transcription and reprogramming factor known to generate induced pluripotent stem cells from target cells did not significantly increase the efficiency of generation of induced pluripotent stem cells by co-expression of both OCT4 and SOX2 in a single vector driven by a strong promoter.

Example 3

Figure 2:
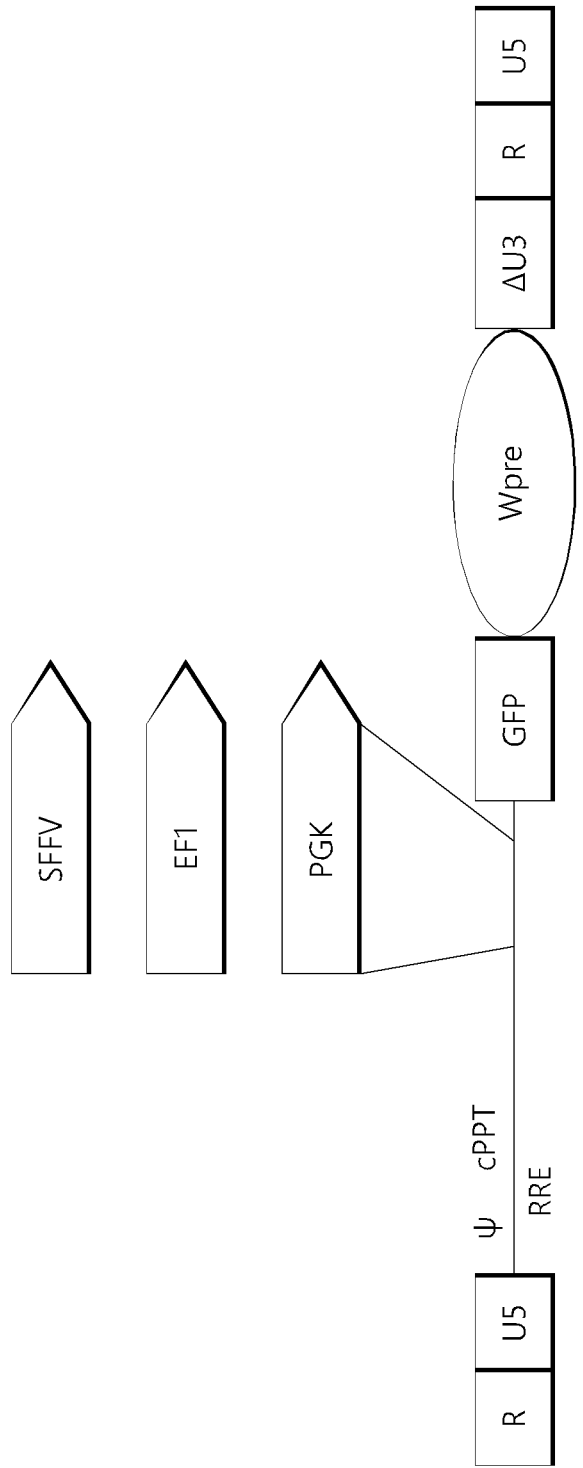
Figure 4:
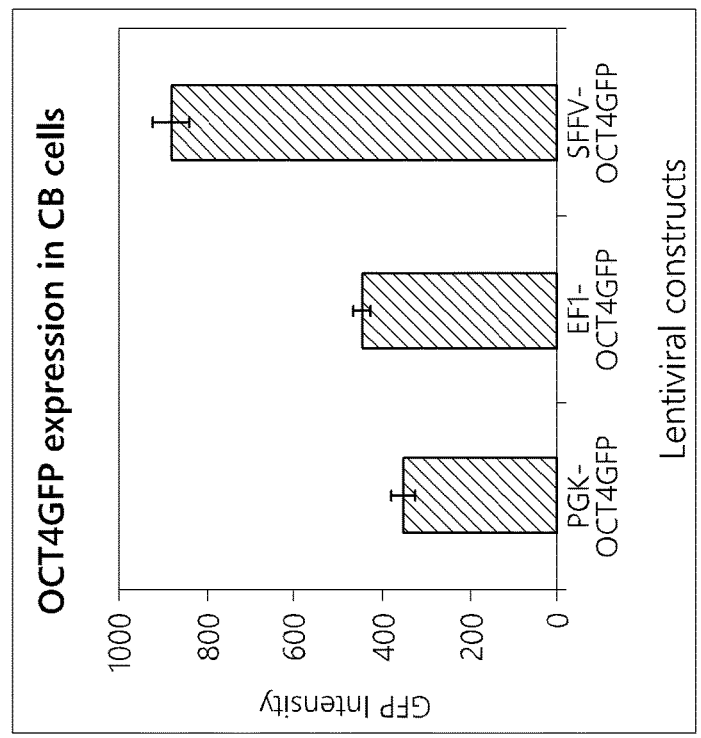
FIG. 4 is a graph of the measured GFP intensity for expression of the fusion gene OCT4GFP driven by the PGK promoter (left), the EF1 promoter (center) or the SFFV promoter (right) in cord blood cells.
Figure 3:
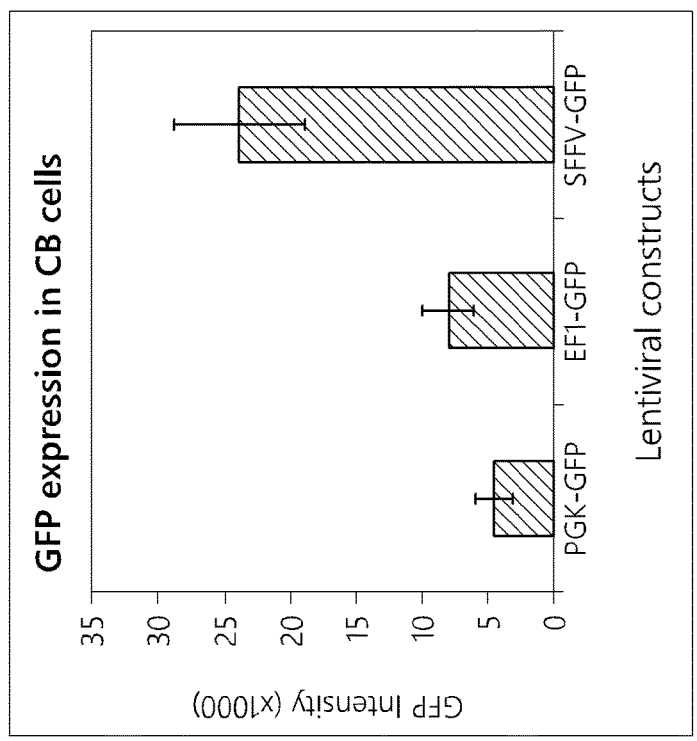
FIG. 3 is a graph of the measured GFP intensity for expression of the GFP driven by the PGK promoter (left), the EF-1 alpha promoter (center) and the SFFV promoter (right) in cord blood cells.

Determination of Whether SFFV Promoter was More Effective in Driving Transgene Expression in Cord Blood CD34+ Cells than Other Promoters The efficiency of generation of induced pluripotent stem cells from cord blood cells from the single vector co-expressing both OCT4 and SOX2 (OS) driven by the spleen focus-forming virus (SFFV) promoter as shown in Example 1 was approximately 1000-fold greater than the efficiency of generation of induced pluripotent stem cells from cord blood CD34+ cells previously reported. Therefore, a determination was next made whether use of the SFFV promoter was partially responsible for the increased efficiency by determining whether the SFFV promoter was more effective in driving transgene expression in cord blood CD34+ cells than other promoters. First, lentiviral vectors were cloned in which green fluorescent protein (GFP) expression was driven by either the phosphoglycerokinase (PGK) promoter, the human elongation factor-1 alpha (EF1 alpha) promoter or the spleen focus-forming virus (SFFV) promoter to determine the relative strength of these promoters in CD34+ cells. Referring now to FIG. 2, there is shown a schematic depiction of the self-inactivating (SIN) lentiviral vector backbones for expression of GFP, where Δ indicates the SIN design with partially deleted U3 of the 3' long terminal repeat, cPPT is a central polypurine tract, Wpre is a post-transcriptional regulatory element, RRE is a rev-responsive element, ψ is a packaging signal, SFFV is the spleen focus-forming virus U3 promoter, EF1 is the Elongation factor-1 alpha promoter and PGK is the phosphoglycerokinase promoter. Cord blood CD+34 cells were transduced with the vectors. Fluorescence-activated cell sorting analysis was performed on the transduced cells. Referring now to FIG. 3, there is shown a graph of the measured GFP intensity for expression of the GFP driven by the PGK promoter (left), the EF-1 alpha promoter (center) and the SFFV promoter (right) in cord blood cells. As can be seen, GFP expression in the cord blood CD34+ cells driven by the PGK promoter was about 20% of the expression driven by the SFFV promoter, and GFP expression in the cord blood CD34+ cells driven by the EF1 promoter was about 35% of the expression driven by the SFFV promoter showing that the SFFV promoter was more than twice as efficient at driving transgene expression than the PGK promoter and the EF1 promoter. Next, a fusion gene of GFP and OCT4 was produced. The fusion gene OCT4GFP was cloned into lentiviral vectors where expression was driven by either the PGK promoter, the EF1 promoter or the SFFV promoter. Cord blood CD+34 cells were transduced with the vectors. Fluorescence-activated cell sorting analysis was performed. GFP expression as measured by fluorescence intensity was assumed to reflect the co-expression level of OCT4. Referring now to FIG. 4, there is shown a graph of the measured GFP intensity for expression of the fusion gene OCT4GFP driven by the PGK promoter (left), the EF1 promoter (center) or the SFFV promoter (right) in cord blood cells. As can be seen, OCT4GFP expression in the cord blood CD34+ cells driven by the PGK promoter was about 35% of the expression driven by the SFFV promoter expression, and OCT4GFP expression in the cord blood CD34+ cells driven by the EF1 promoter was about 50% of the expression driven by the SFFV promoter showing that the SFFV promoter was significantly more efficient at driving transgene expression than the PGK promoter and the EF1 promoter. Therefore, the SFFV promoter was at least twice as effective in driving transgene expression in cord blood CD34+ cells as the PGK promoter and the EF1 promoter.

Example 4

Determination of Whether Transgene Expression Level Affected Generation of Induced Pluripotent Stem Cells Then, a determination was made as follows, whether the increased level of transgene expression from the SFFV promoter demonstrated in Example 3 had an effect on the generation of induced pluripotent stem cells from cord blood CD34+ cells. $1\times10^4$ cord blood CD34+ cells were transduced with a single lentiviral vector mediating overexpression of both OCT4 and SOX2 (OS transgene) driven by either the phosphoglycerokinase (PGK) promoter, the human elongation factor-1 alpha (EF1 alpha) promoter or the spleen focus-forming virus (SFFV). In six independent experiments, no induced pluripotent stem cells were generated from the transduced cells where the OS transgene was driven by either the PGK promoter or by the EF1 promoter, while approximately 200 colonies were generated from 10,000 CD34+ cells using the SFFV promoter. Given that expression of OCT4 was decreased by about 50% when driven by the EF1 promoter as compared to the SFFV promoter (Example 3), these experiments indicate that a 50% decrease in OS expression leads to failure to generate induced pluripotent stem cells from the transduced cord blood CD34+ cells. Further, a synthetic OS transgene (synOS) was synthesized that was codon optimized (DNA 2.0, Menlo Park, Calif., US) and expressed in a lentiviral vector driven by the SFFV promoter. Analysis of protein expression indicated that the level of the protein encoded by synOS was about 20% lower than the level of the protein encoded by the wild type OS, while the number of induced pluripotent stem cell colonies generated by the cord blood CD34+ cells transduced with the synOS vector was about 25% of the number of induced pluripotent stem cell colonies generated by the cord blood CD34+ cells transduced with the vector comprising the wild-type OS. Combined with the data above, these experiments show that a 20% drop in protein level from expression of transgene resulted in generation of only 25% efficiency of induced pluripotent stem cells generation while a 50% drop in expression of transgene resulted in failure to generate any induced pluripotent stem cell colonies. Therefore, the level of OS transgene expression is critical to generation of induced pluripotent stem cells from cord blood CD34+ cells.

Example 5

Determination of Whether Additional Transcription and Reprogramming Factors Increased the Efficiency of Generation of Induced Pluripotent Stem Cells Using Co-Expression of OCT4 and SOX2 in a Viral-Based Vector Next, a determination was made as follows, whether adding transcription and reprogramming factor genes beside oct4 and sox2 to the viral-based vector affected the transgene expression level needed to generate induced pluripotent stem cells. The two additional transcription and reprogramming factors tested were myc and klf4, both of which have previously been shown to generate induced pluripotent stem cells from hematopoietic stem cells in various vectors. Lentiviral vectors were produced where one vector mediated overexpression of both OCT4 and SOX2 driven by the EF1 promoter, and one vector mediated overexpression of MYC driven by the SFFV promoter. Referring now to FIG. 5, there is shown a graph of the number of induced pluripotent stem cell colonies generated from $1\times10^4$ cord blood CD34+ cells that were transduced only with the vector mediating overexpression of both OCT4 and SOX2 driven by the EF1 promoter (left), transduced with both the vector mediating overexpression of both OCT4 and SOX2 driven by the EF1 promoter and the vector mediating overexpression of MYC driven by the SFFV promoter (center), and transduced only with the vector mediating overexpression of MYC driven by the SFFV promoter (right). As can be seen, no induced pluripotent stem cells were generated from the cells transduced only with the vector mediating overexpression of both OCT4 and SOX2 driven by the EF1 promoter (left), or transduced only with the vector mediating overexpression of MYC driven by the SFFV promoter (right). However, induced pluripotent stem cells were generated from 0.1% of the cells that were transduced with both the vector mediating overexpression of both OCT4 and SOX2 driven by the EF1 promoter and with the vector mediating overexpression of MYC driven by the SFFV promoter (center). Analysis of alkaline phosphatase (ALP) staining and fluorescence-activated cell sorting (FACS) of the generated induced pluripotent stem cells did not show any obvious differences in the expression of pluripotency markers when compared with induced pluripotent stem cells generated from cells transduced with a vector mediating overexpression of both OCT4 and SOX2 driven by the SFFV promoter, as above. Further, cord blood CD34+ cells were transduced with a vector mediating overexpression of both MYC and KLF4 driven by the EF1 promoter, but no induced pluripotent stem cells were generated from the cells. Therefore, these experiments show that high-level expression of OCT4 and SOX2 (driven by the SFFV promoter, Examples 1 and 4) without other transcription and reprogramming factors is sufficient to generate induced pluripotent stem cells from cord blood CD34+ cells using a viral-based vector, while lower-level expression of OCT4 and SOX2 (driven by the EF1 promoter (Example 5) requires additional transcription and reprogramming factors to generate induced pluripotent stem cells from cord blood CD34+ cells using a viral-based vector.

Example 6

Determination of Whether Co-Expression of OCT4 and SOX2 in a Nonviral Vector Generates Induced Pluripotent Stem Cells Then, a determination was made as follows, whether co-expression of OCT4 and SOX2 in a nonviral vector generates induced pluripotent stem cells from cord blood CD34+ cells, such as for example, co-expression of OCT4 and SOX2 in an episomal vector. Referring now to FIG. 6, there is shown a schematic depiction of an episomal mammalian expression vector backbone (bottom) for (from upper to lower, respectively) co-expression of OCT4 and SOX2 (OS) without Wpre (pCEP-OS (w/o W)), co-expression of OCT4 and SOX2 (OS) with Wpre (pCEP-OS), expression of KLF4 (K) (pCEP-K), and expression of MYC (MK) (pCEP-MK); where 2a is a self-cleavage site derived from equine rhinitis A virus, Wpre is a post-transcriptional regulatory element, SV40PolyA is a polyadenylation signal from SV40 virus, OriP is an EBV origin of replication, and EBNA1 is Epstein-Barr nuclear antigen 1 which plays essential roles in replication and persistence of episomal DNA in infected cells. First, the OCT4 and SOX2 (OS) transgene driven by the SFFV promoter was shuttle cloned from the lentiviral vector (Examples 1 and 4) into the EBNA1/OriP-based episomal mammalian expression vector (Invitrogen), where the hygromycin resistance gene element and CMV promoter were removed from the pCEP4 vector by digestion with endonucleases NruI and BamHI, and inserts were cut from the counterparts of lentiviral vectors. Then, $1 \times 10^5$ cord blood CD34+ cells were cultured in IMDM/10% FBS supplemented with the cytokines FlT3-ligand (FL), stem cell factor (SCF) and thrombopoietin (TPO) at 100 ng/ml. Three days later, cells were harvested for nucleofection with a total of 12 ug episomal vector. Nucleofection was performed with Amaxa Nucleofector II using program U-008 Immediately after nucleofection, the cells were cultured in a CH-296 pretreated well plate to facilitate the cord blood cell recovery. The next day, half of the cells were transferred to each well of MEF-coated six-well plates. The cells were cultured the same way as for reprogramming with lentiviral vector, above. The total number of induced pluripotent stem cell colonies was counted on day sixteen post-transfection after ALP staining. At day fourteen to seventeen, colonies were picked for further culture or harvested for FACS analysis. After three days of culture, the total cell number increased by about five-fold and all the cells were harvested for nucleofection with the pCEP-OS (w/o W) vector. No induced pluripotent stem cells were generated in three independent attempts. Next, the post-transcriptional regulatory element Wpre was cloned into the pCEP-OS (w/o W) vector producing the pCEP-OS episomal vector to enhance transgene expression levels to determine whether the failure to generate induced pluripotent stem cells by the pCEP-OS (w/o W) vector was due to low OS transgene expression levels mediated by the pCEP-OS (w/o W) vector. HE 293T cells were transfected with same amount of the pCEP-OS episomal vector. Referring now to FIG. 7, there are shown, respectively, graphs of the relative expression of OCT4 (left) and SOX2 (right) for cells transfected with pCEP-OS (w/o Wpre) (left bar) and pCEP-OS (with Wpre) (right bar). As can be seen, the inclusion of Wpre in the episomal vector led to a 50% increase in OCT4 expression (right graph) and a 55% increase in SOX2 expression (left graph), P<0.05. Then, $1 \times 10^5$ freshly thawed cord blood CD34+ cells were transfected with the pCEP-OS episomal vector and generated about twenty induced pluripotent stem cell colonies from the progeny. Therefore, co-expression of OCT4 and SOX2 driven by SFFV alone in a nonviral vector such as an episomal vector generated induced pluripotent stem cells from cord blood CD34+ cells.

Example 7

Determination of Whether Additional Transcription and Reprogramming Factors Increased the Efficiency of Generation of Induced Pluripotent Stem Cells Using Co-Expression of OCT4 and SOX2 in a Nonviral Vector Next, a determination was made as follows, whether additional transcription and reprogramming factors increased the efficiency of generation of induced pluripotent stem cells using co-expression of OCT4 and SOX2 in a nonviral vector. The test transcription and reprogramming factors used was KLF4 (Krueppel-like factor 4 encoded by klf4) (K) and MYC (encoded by myc; c-myc) (MK). $1 \times 10^5$ cord blood CD34+ cells were transfected with the pCEP-OS episomal vector (OS), with the pCEP-OS episomal vector and the pCEP-K episomal vector (OS+K), or with the pCEP-OS episomal vector and the pCEP-MK episomal vector (OS+MK). Referring now to FIG. 8, there is shown a graph of the number of induced pluripotent stem cells generated from $1 \times 10^5$ cord blood CD34+ cells transfected with the pCEP-OS episomal vector (OS) (left-most bar), with the pCEP-OS episomal vector and the pCEP-K episomal vector (OS+K) (center bar), or with the pCEP-OS episomal vector and the pCEP-MK episomal vector (OS+MK) (right-most bar). As can be seen, the cells transfected with (OS+K) generated eight times the number of induced pluripotent stem cells as the cells transfected with OS only, and the cells transfected with (OS+MK) generated twenty-four times the number of induced pluripotent stem cells as the cells transfected with OS only (OS vs. OS+K: P<0.05; OS+K vs. OS+MK: P<0.05). Further, the appearance of the first induced pluripotent-like stem cell colonies was observed at nine to ten days, six to seven days and four to five days after transfection with OS, OS+K, and OS+MK, respectively. Additionally, $1 \times 10^5$ cord blood CD34+ cells transfected with the pCEP-OS+MK episomal vector generated approximately six hundred induced pluripotent stem cells compared with about eighty colonies from the same amount of cord blood CD34+ cells even with 5 factors (OSMK+LIN28) using the EF1 promoter. Further, the induced pluripotent stem cells generated from the cord blood CD34+ cells transfected with the nonviral vectors OS, OS+K, and OS+MK were tested with immunostaining and fluorescence-activated cell sorting (FACS) analysis twenty days after nucleofection to determine differences in the expression of pluripotency markers. 20-30% of the cells expressed the induced pluripotent stem cells markers NANOG and TRA-1-60 in all the cells groups, however, while the cells transfected with OS+MK had significantly less Tra-1-60 positive induced pluripotent stem cells (22%) than cells transfected with OS (30%) or with OS+K (31%). Therefore, additional transcription and reprogramming factors increased the efficiency of generation of induced pluripotent stem cells using co-expression of OCT4 and SOX2 in a nonviral vector; however, additional transcription and reprogramming factors do not necessarily increase the expression of pluripotency markers in the generated cells.

Example 8

Determination of Whether Co-Expression of OCT4 and SOX2 in a Nonviral Vector Generates Functional Transgene-Free Induced Pluripotent Stem Cells Then, a determination was made as follows, whether co-expression of OCT4 and SOX2 in a nonviral vector generates functional transgene-free induced pluripotent stem cells. Ten induced pluripotent stem cell colonies were randomly picked from the colonies generated from cord blood CD34+ cells as above (Example 6), and were passaged for more than three months. Real-time analysis conducted using two pairs of primers demonstrated that no copies of the vector for one primer were detected in any cell, and approximately 0.5 copies of the vector for the other primer were detected per cell. After eight passages, the average copy number of residual vector decreased to 0.001-0.007 copies per genome using either primer and in two of ten clones, the vector was undetectable. After twelve passages, vector was undetectable using either primer in the majority of the clones. Further, several of the clones were randomly picked and characterized. Immunostaining showed that all clones expressed typical human induced pluripotent stem cells transcription factors OCT4, SOX2, NANOG, and surface markers SSEA-3, SSEA-4 and Tra-1-60. Karyotype analysis indicated that all clones possessed a normal human karyotype. Sulphite sequencing showed that both the OCT4 and NANOG promoters were demethylated in 3 randomly picked induced pluripotent stem cells. Induced pluripotent stem cells formed teratomas consisting of derivatives of all three embryonic germ layers when injected into immunodeficient NOD scid IL2 receptor gamma chain knockout (NSG) mice, demonstrating the pluripotency of the induced pluripotent stem cells. Therefore, co-expression of OCT4 and SOX2 in a nonviral vector generates transgene-free induced pluripotent stem cells that appear to be morphologically, phenotypically and functionally identical to pluripotent stem cells.

Example 9

Determination of Whether Expression of BCL-XL in a Viral Vector Increases the Efficiency of OCT4/SOX2-Mediated Reprogramming of Cord Blood CD34+ Cells into Induced Pluripotent Stem Cells Next, a determination was made as follows, whether simultaneous expression of an anti-apoptotic factor selected from the group consisting of BCL2, BCL-XL (an isoform of Bcl-X(L) of BCL2L1) and MCL1, along with balanced expression of OCT4 and SOX2 (OS) in a lentiviral vector increases reprogramming efficiency of cord blood CD34+ cells into induced pluripotent stem cells (iPSCs). The BCL2, BCL-XL, or MCL1 genes were each cloned into a lentiviral vector under the control of the spleen focus-forming virus (SFFV) promoter. Cord blood CD34+ cells were cultured for two days before lentiviral transduction. Cord blood iPSC colonies were enumerated at two weeks after transduction of reprogramming factors. Referring now to FIG. 9, there is shown a graph of the number of induced pluripotent stem colonies generated from $1 \times 10^4$ cord blood CD34+ cells when reprogrammed by using balanced expression of OCT4 and SOX2 (OS) (left-most bar), OS+BCL2 (center left bar), OS+BCL-XL (center right bar), and OS+MCL (right-most bar). Data shown are presented as mean±SEM (n=4). * indicates P<0.05. As can be seen, between 1 and 2% of cord blood CD34+ cells were reprogrammed to iPSCs using balanced expression of OCT4 and SOX2 (OS) (left-most bar) only. Inclusion of BCL2 or BCL-XL increased reprogramming efficiency by approximately three-fold (P<0.05), while the inclusion of MCL1 had no apparent enhancing effect on OS-mediated reprogramming efficiency. While the inclusion of BCL-XL demonstrated increased reprogramming efficiency over the inclusion of BCL2, as shown, but the difference in efficiency was not statistically significantly. Therefore, inclusion of either BCL2 or BCL-XL significantly increases efficiency of OCT4/SOX2-mediated reprogramming of cord blood CD34+ cells.

Example 10

Determination of Whether BCL-XL Increases the Efficiency of OCT4/SOX2-Mediated Reprogramming of Adult Peripheral Blood Mononuclear Cells Then, a determination was made as follows, whether simultaneous expression of an anti-apoptotic factor selected from the group consisting of BCL2, BCL-XL and MCL1, along with balanced expression of OCT4 and SOX2 (OS) in a lentiviral vector increases reprogramming efficiency of adult peripheral blood mononuclear cells (PB MNCs) into induced pluripotent stem cells (iPSCs). The BCL2, BCL-XL, or MCL1 gene was each cloned into a lentiviral vector under the control of the spleen focus-forming virus (SFFV) promoter. Adult peripheral blood mononuclear cells were isolated from several male and female donors aged 22 to 43 years old by Ficoll-Hypaque density gradient centrifugation or were purchased from AllCells (Emeryville, Calif., US), and cultured for four to six days. To generate adult peripheral blood iPSCs, the human peripheral blood mononuclear cells were cultured in hematopoietic stem cell (HSC) culture conditions. Iscove's modified Dulbecco's medium (IMDM)/ 10% fetal bovine serum (FBS), supplemented with TPO, SCF, FL, and G-CSF (purchased from ProSpec, East Brunswick, N.J., US; and StemRegenin1 (SRL Cellagen Technology, San Diego, Calif., US), each at 10 ng/ml, IL-3 at 10 ng/ml. After six to eight days of culture, $1 \times 10^5$ cells per culture well were seeded into non-tissue culture-treated 24-well plates that were pre-coated with fibronectin fragment RetroNectin or CH-296 (Takara Bio, Inc., Shiga, Japan). The cells were then transduced with a lentiviral vector co-expressing OCT4 and SOX2, along with or without a lentiviral vector expressing BCL2, BCL-XL, or MCL1, with a multiplicity of infection (MOI) of four. One day after viral transduction, cells were harvested and transferred to 6-well culture plates, which were pre-seeded with inactivated rat embryonic fibroblasts (REF) feeder cells (Applied Biological Materials (ABM), Richmond, BC, Canada). The cells were maintained in the HSC culture condition for two additional days before being gradually replaced with iPSC medium, which comprised Knockout DMEM/F12 medium (Invitrogen, Carlsbad, Calif., US) supplemented with 20% Knockout Serum Replacement (KSR) (Invitrogen), 1 mM GlutaMAX (Invitrogen), 2 mM nonessential amino acid (ABM), 1× penicillin/streptomycin (ABM), 0.1 mM β-mercaptoethanol (Sigma), 20 ng/ml FGF2 (ABM), and 50 μg/ml ascorbic acid. The culture medium was changed to fresh medium every two days. To increase reprogramming efficiency, an inhibitor of histone deacetylase sodium butyrate was added at 0.25 mM every two days from day two to day ten, and the cells were cultured under hypoxia throughout the reprogramming procedure by placing cells in culture plates in a hypoxia chamber (Stemcell Technologies, Inc., Vancouver, BC, Canada) that was flushed with mixed air composed of 92% $N_2$/3% $O_2$/5% $CO_2$. Starting from day ten, only REF-conditioned medium was used in the culture. The peripheral blood mononuclear cell iPSC colonies were enumerated at three weeks after transduction of reprogramming factors.

Referring now to FIG. 10, there is shown a graph of the number of induced pluripotent stem colonies generated from $1\times10^5$ peripheral blood mononuclear cells when reprogrammed by using balanced expression of OCT4 and SOX2 (OS) (left-most), OS+BCL2 (center left), OS+BCL-XL (center right), and OS+MCL (right-most). Data shown are presented as mean±SEM (n=4). * indicates P<0.05. As can be seen, while OS alone could also induce adult peripheral blood mononuclear cells into pluripotency, the efficiency was 100-fold lower than the efficiency of reprogramming of cord blood CD34+ cells. Inclusion of BCL2 or BCL-XL increased reprogramming efficiency by approximately three-fold (P<0.05), while the inclusion of MCL1 had no apparent enhancing effect on OS-mediated reprogramming efficiency. While the inclusion of BCL-XL demonstrated increased reprogramming efficiency over the inclusion of BCL2, as shown, the difference in efficiency was not statistically significantly. As can be seen, the relative efficiency of the three anti-apoptotic factors on OS-mediated reprogramming of peripheral blood mononuclear cells (FIG. 10) were identical to that of cord blood CD34+ cells (FIG. 9). Therefore, inclusion of either BCL2 or BCL-XL significantly increases efficiency of OCT4/SOX2-mediated reprogramming of adult peripheral blood mononuclear cells.

Example 11

Determination of Whether Co-Expression of OCT4 and SOX4 in an Episomal Vector Generates Induced Pluripotent Stem Cells from Adult Peripheral Blood Mononuclear Cells, and Whether Co-Expression of BCL-XL in the Episomal Vector Increases the Efficiency of OCT4/SOX2-Mediated Reprogramming of Adult Peripheral Blood Mononuclear Cells into Induced Pluripotent Stem Cells Next, a determination was made as follows, whether balanced expression of OCT4 and SOX2 in a single episomal (nonviral) vector, generates induced pluripotent stem cells from adult peripheral blood mononuclear cells. Referring now to FIG. 11, there are shown, respectively, a schematic depiction of an episomal mammalian expression vector backbone (bottom) for (from upper to lower, respectively) co-expression of OCT4 and SOX2 (pCEP-OS), expression of KLF4 (pCEP-K), expression of BCL-XL (pCEP-B), co-expression of BCL-XL and KLF4 (pCEP-BK), co-expression of OCT4, SOX2, BCL-XL and KLF4 (pCEP-OSBK), and co-expression of MYC and KLF4 (pCEP-MK), where 2a is a self-cleavage site derived from equine rhinitis A virus, SFFV is a spleen focus-forming virus promoter, Wpre is a post-transcriptional regulatory element, SV40PolyA is a polyadenylation signal from SV40 virus, OriP is an EBV origin of replication, and EBNA1 is Epstein-Barr nuclear antigen 1 (FIG. 11A); photographs of alkaline phosphatase staining (a measure of pluripotency) of induced pluripotent stem cell colonies at four weeks after nucleofection of adult peripheral blood mononuclear cells with episomal vectors expressing reprogramming factors OCT4 and SOX2 (OS) (left-most); OCT4, SOX2 and BCL-XL (OS+B) (center left); OCT4, SOX2, MYC and KLF4 (OS+MK) (center right), and OCT4, SOX2, MYC, KLF4 and BCL-XL (OS+MK+B) (right most) (FIG. 11B); a graph of the number of induced pluripotent stem colonies generated from 1 ml of adult peripheral blood mononuclear cells nucleofected with the episomal vectors expressing reprogramming factors OCT4 and SOX2 (OS) without BCL-XL/with BCL-XL (left-most two bars); and OCT4, SOX2 and KLF4 (OS+K) without BCL-XL/with BCL-XL (center two bars); and OCT4, SOX2, MYC and KLF4 (OS+MK) without BCL-XL/with BCL-XL (right-most two bars) (data are presented as mean±SEM (n=6), where * indicates P<0.05) (FIG. 11C). As indicated in Example 6, episomal vector constructs comprising only the two transcription and reprogramming factor genes OCT4 and SOX2 successfully generated integration-free induced pluripotent stem cells from cord blood CD34+ cells. To test the effect of the various transcription and reprogramming factor genes on generation of integration-free induced pluripotent stem cells from adult peripheral blood mononuclear cells (PB MNCs), adult peripheral blood mononuclear cells were cultured for four to eight days in conditions that favored expansion of hematopoietic stem cells and myeloid cells before nucleofection, and then nucleofected with the various vectors shown in FIG. 11A. After nucleofection of cultured peripheral blood mononuclear cells with the various episomal vectors, $1\times10^6$ cells were transferred to 6-well plates, pre-coated with feeder cells, for three to four weeks of culture. Referring now to FIG. 11B and FIG. 11C, in contrast to cord blood CD34+ cells (Example 6), episomal vectors expressing OCT4 and SOX2 alone (OS) essentially failed to reprogram peripheral blood mononuclear cells (FIG. 11B (left-most) and FIG. 11C (left)) in any significant amount, while inclusion of BCL-XL along with OCT4 and SOX2 in the episomal vector successfully reprogrammed the peripheral blood mononuclear cells (FIG. 11B (center left) and FIG. 11C (left)). Further as can be seen, the addition of KLF4, or KLF4 and MYC without BCL-XL did reprogram some peripheral blood mononuclear cells into induced pluripotent stem cells (FIG. 11C (center and right)) in small amounts. Further as can be seen, inclusion of BCL-XL in the episomal vectors OS+K and OS+MK also reprogrammed the peripheral blood mononuclear cells into induced pluripotent stem cells (FIG. 11B (right-most) and FIG. 11C (center and right)), where the inclusion of BCL-XL increased reprogramming efficiency by up to 10-fold over to 10 iPSC colonies per ml of peripheral blood mononuclear cells. The inclusion of MYC, however, along with OCT4, SOX2, KLF4 and BCL-XL did not further increase the efficiency of generation of induced pluripotent stem cells from peripheral blood mononuclear cells beyond that of using OCT4, SOX2, KLF4 and BCL-XL alone (FIG. 12C (right)).

Example 12

Determination of Optimal Cell Population for Generation of Induced Pluripotent Stem Cells from Adult Peripheral Blood Mononuclear Cells Then, a determination was made as follows, of the optimal cell population for generation of induced pluripotent stem cells from adult peripheral blood cells. Referring now to FIG. 12, there are shown, respectively, photographs of alkaline phosphatase staining of induced pluripotent stem cell colonies at four weeks after nucleofection of fractionated adult peripheral blood mononuclear cells with episomal vectors expressing reprogramming factors OCT4, SOX2, MYC, KLF4 and BCL-XL (OS+MK+B), where the fractionated adult peripheral blood mononuclear cells expressed the myeloid lineage marker CD33 (CD33+, left-most), did not express the myeloid lineage marker CD33 (CD33−, center left), expressed the T cell marker CD3 or the B cell marker CD19 (CD3+/CD19+, center right), and did not express the T cell marker CD3 or the B cell marker CD19 (CD3−/CD19−, right-most) (FIG. 12A); and a graph of the number of induced pluripotent stem colonies generated from 1 ml of adult whole peripheral blood mononuclear cells nucleofected with the episomal vectors expressing OCT4, SOX2, MYC, KLF4 and BCL-XL (left bar), and generated from 1 ml of adult peripheral blood mononuclear cells that were T cell/B cell lymphocyte depleted (CD3−/CD19−) nucleofected with the episomal vectors expressing OCT4, SOX2, MYC, KLF4 and BCL-XL (right bar), (data are presented as mean±SEM (n=4), where * indicates P<0.05) (FIG. 12B). As can be seen, nucleofection of fractionated adult peripheral blood mononuclear cells with episomal vectors expressing reprogramming factors OCT4, SOX2, MYC, KLF4 and BCL-XL (OS+MK+B) generated induced pluripotent stem cells from cells expressing the myeloid lineage marker CD33 (CD33+, FIG. 12A, left-most), but not from cells that did not express the myeloid lineage marker CD33 (CD33−, FIG. 12A, center left). Further, nucleofection of fractionated adult peripheral blood mononuclear cells with episomal vectors expressing reprogramming factors OCT4, SOX2, MYC, KLF4 and BCL-XL (OS+MK+B) did not generate induced pluripotent stem cells from cells that expressed the T cell marker CD3 or the B cell marker CD19 (CD3+/CD19+, FIG. 12A, center right), but did generate induced pluripotent stem cells from cells that did not express the T cell marker CD3 or the B cell marker CD19 (CD3−/CD19−, FIG. 12A, right-most). Quantifying these results indicated that depleting the adult whole peripheral blood mononuclear cells of cells that expressed the T cell marker CD3 or the B cell marker CD19 (CD3−/CD19−) increased the generation of induced pluripotent stem cells by about ten-fold (on a per cell basis, where only about 30% of the peripheral blood mononuclear cells were left after purification to delete cells that expressed the T cell marker CD3 or the B cell marker CD19 (CD3−/CD19−)) (FIG. 12B). Therefore, integration-free induced pluripotent stem cells can be generated from non-lymphoid cells, and in particular, from T cell and B cell-depleted non-lymphoid cells.

Example 13

Determination of Optimal Culture Duration Before Nucleofection for the Generation of Induced Pluripotent Stem Cells from Adult Peripheral Blood Mononuclear Cells Next, a determination was made as follows, of the optimal culture duration before nucleofection for the generation of induced pluripotent stem cells from adult peripheral blood mononuclear cells. Based on the results from Example 11, peripheral blood mononuclear cells depleted of cells that expressed the T cell marker CD3 or the B cell marker CD19 (CD3−/CD19− cells) were used to determine the optimal culture duration before nucleofection for reprogramming. The numbers of induced pluripotent stem cell colonies were counted at three to four weeks after nucleofection. Referring now to FIG. 13, there is shown a graph of the number of induced pluripotent stem cell colonies generated from 1 ml of adult peripheral blood mononuclear cells that were depleted of cells that expressed the T cell marker CD3 or the B cell marker CD19 (CD3−/CD19−), and were then nucleofected with the episomal vectors expressing OCT4, SOX2, MYC, KLF4 and BCL-XL versus the number of days in culture before nucleofection (data are presented as mean±SEM (n=6), where * indicates P<0.05). As can be seen, when the days cultured before nucleofection was two days or eight days, only a few induced pluripotent stem cell colonies were obtained, whereas culturing the cells for four days before nucleofection resulted in optimal generation of induced pluripotent stem cells of more than twenty iPSC colonies from 1 ml of cells. This optimal culture duration is consistent with analysis showing that more progenitors (CD34+ cells) were expanded after four to six days of culture, while culturing for a longer duration led to differentiation of myeloid progenitors (data not shown). Therefore, the optimal culture duration before nucleofection for the generation of induced pluripotent stem cells from adult peripheral blood mononuclear cells depleted of cells that expressed the T cell marker CD3 or the B cell marker CD19 (CD3−/CD19−) is about four days.

Example 14

Determination of Morphology, Phenotype and Function of Induced Pluripotent Stem Cells Generated from Adult Peripheral Blood with Integration-Free Yamanaka Factors Then, a determination was made as follows, of the morphology, phenotype and function of integration-free induced pluripotent stem cells generated from adult peripheral blood mononuclear cells depleted of cells that expressed the T cell marker CD3 or the B cell marker CD19 (CD3−/CD19− cells) using integration-free Yamanaka factors in accordance with Example 12 and Example 13. The generated integration-free induced pluripotent stem cells were robustly proliferated under human induced pluripotent stem cells culture conditions for more than twenty passages. Referring now to FIG. 14, there are shown, respectively, a photograph of a representative induced pluripotent stem cell colony (FIG. 14A); a photograph of a representative karyogram of an induced pluripotent stem cell clone (FIG. 14B); representative images captured using a Zeiss LSM 710 confocal microscope with a 20× objective of induced pluripotent stem cells immunostained to show expression of pluripotency markers OCT4 (left), SOX2 (center), and NANOG and SSEA4 (right) by representative induced pluripotent stem cell colonies (FIG. 14C); representative images captured using an Olympus microscope with a 20× objective of cell layer derivatives in hematoxylin and eosin (H & E) staining formed by teratomas in immunodeficient mice produced by representative induced pluripotent stem cell colonies, where the teratoma cell layers included all three embryonic germ layers, cartilage (mesoderm, left), glands (endoderm, center) and neurotubules (ectoderm, right) (FIG. 14D); photographs of representative induced pluripotent stem cell colonies showing differentiation into mesenchymal stem cells (leftmost), stained with Oil Red O stains to show the oil droplets of adipocytes (center left), stained with Alizarin Red to show bone nodules formed by osteoblasts (center right), and stained with Alcian Blue to show acid mucopolysaccharides synthesized and secreted by chondrocytes (right-most) (FIG. 14E); photographs of representative induced pluripotent stem cell colonies showing differentiation into hepatocytes (left-most), and stained with monoclonal antibody against alpha-fetoprotein (AFP) to show expression of alpha-fetoprotein (center left), stained with goat anti-albumin to show expression of albumin (ALB), and stained with goat anti-alpha 1-antitrypsin to show expression of alpha 1-antitrypsin (a1-AT) (FIG. 14F); and a photograph of representative induced pluripotent stem cell colonies showing expression of Troponin I marker showing differentiation into cardiomyocytes where the cell nuclei are counterstained with 4',6-diamidino-2-phenylindole (FIG. 14G).

As can be seen, the integration-free induced pluripotent stem cells showed typical morphology for human pluripotent stem cells (FIG. 14A). Further, karyotyping and Giemsa banding (GTG-banding) chromosome analysis were carried out on representative induced pluripotent stem cell clones following standard DNA spectral karyotyping procedures using HiSKY Complete Cytogenetic System (Applied Spectral Imaging, Inc., Vista, Calif., US). For each clone, 10 metaphases were analyzed and karyotyped. As can be seen in the representative karyogram, FIG. 14B, all integration-free induced pluripotent stem cell clones were normal. Additionally, the integration-free induced pluripotent stem cells were cultured in chamber slides for four to five days. The cells were then treated with fixation buffer and permeabilization buffer (eBioscience, Inc., San Diego, Calif., US) for thirty minutes before being stained overnight at 4° C. with PE or FITC conjugated antibodies anti-OCT4 (eBioscience), anti-SOX2 (BD Pharmingen; San Diego, Calif., US), anti-NANOG (BD Pharmingen), and anti-SSEA-4 (eBioscience). Confocal imaging was performed using the Zeiss LSM 710 NLO laser scanning confocal microscope with a 20× objective. High resolution monochrome images were captured using a Zeiss HRm CCD camera. As can be seen in FIG. 14C, the integration-free induced pluripotent stem cells expressed the pluripotency markers OCT4, SOX2, NANOG and SSEA4. Further, immunodeficient NSG mice (purchased from the Jackson Laboratory, Sacramento, Calif., US) were injected subcutaneously with $1 \times 10^6$ integration-free induced pluripotent stem cells according to the present invention that were suspended in 200 ul DMEM/F12 diluted (1:1) Matrigel solution (BD) and the cells formed teratomas. Two months after injection, the teratomas were dissected, fixed in 10% formalin, stained with hematoxylin and eosin, and examined by a board certified pathologist. The teratomas and were found to contain derivatives of all three embryonic germ layers as represented by cartilage (mesoderm, left), glands (endoderm, center) and neurotubules (ectoderm, right) (FIG. 14D) indicating that these integration-free induced pluripotent stem cells automatically differentiated into tissues and cells of mesoderm, endoderm and ectoderm after implantation in animals cells.

Induced pluripotent stem cells according to the present invention were then investigated to determine if the integration-free induced pluripotent stem cells could differentiate into cells of different lineages in culture. First, integration-free induced pluripotent stem cells were cultured with Mesenchymal Stem Cell (MSC) Medium Kit (ABM) for four to five days. The cells were then treated with Accutase (Innovative Cell Technologies, Inc., San Diego, Calif., US) and further cultured in fibronectin (BD)-pre-coated non-tissue culture treated well plates and readily differentiated into mesenchymal stem cells (MSCs) as can be seen in FIG. 14E (left-most), where more than 90% of the differentiated cells expressed typical markers of mesenchymal stem cells including CD73, CD105 and CD166. After three weeks of culture in differentiation medium, the mesenchymal stem cells were stained with Oil Red O, Alizarin Red, and Alcian Blue, showing differentiation into adipocytes, osteoblasts and chondrocytes (FIG. 14E, center left, center right and right-most, respectively). These data suggest that the mesenchymal stem cells differentiated from integration-free induced pluripotent stem cells are morphologically and functionally indistinguishable to bone marrow-derived mesenchymal stem cells. Second, integration-free induced pluripotent stem cells were cultured under conditions that produced hepatocytes. Initially, induction of the integration-free induced pluripotent stem cells definitive endoderm (DE) was initiated in RPMI 1640 medium containing 100 ng/ml Activin A (R&D Systems, Minneapolis, Minn., US) and 2 mM L-glutamine for two days. B27 (Invitrogen) and 0.5 mM sodium butyrate were then supplemented for additional seven to nine days. The definitive endoderm cells were treated with Accutase for a short period of time and rapidly transferred to collagen I-coated plates and cultured in RPMI 1640 medium supplemented with FGF-4, HGF, BMP2, BMP4 (R&D Systems), dexamethasone, and DMSO. Fourteen days after differentiation induction, the cells were maintained in hepatocyte culture medium supplemented with FGF-4, HGF, Oncostatin M (R&D Systems), dexamethasone and DMSO for an additional two to three weeks. At eighteen days after differentiation, cells were stained with monoclonal antibody against AFP (Dako North America, Inc., Carpinteria, Calif., US), goat anti-albumin (Bethyl Laboratories, Inc., Montgomery, Tex., US), and goat anti-alpha 1-antitrypsin (Bethyl), following standard protocols. Successful differentiation into hepatocytes was evidenced by a series of morphological changes resulting in a polygonal shape and round single or double nuclei with many cytoplasmic vesicles characteristic of mature hepatocytes, as can bee seen in FIG. 14F. Immunohistochemical analysis showed that about 90% of the differentiated cells expressed liver-specific genes at eighteen days after culture, including alpha fetoprotein (AFP), albumin (ALB), and alpha 1-antitrypsin ($\alpha$1-AT) (FIG. 14F, center left, center right and right-most, respectively), further indicating differentiation into mature hepatocytes. Third, integration-free induced pluripotent stem cells were cultured under conditions that produced cardiomyocytes. Small clusters of integration-free induced pluripotent stem cells were cultured in differentiation medium consisting of StemPro-34 (Invitrogen), supplemented with 2 mM GlutaMAX, 50 µg/ml ascorbic acid, and $4 \times 10^{-4}$ M monothioglycerol (MTG) (Sigma). Cytokine Activin A (R &D Systems) was used at 50 ng/ml for one day and 10 ng/ml BMP4 (R&D Systems) was added for four days. After twelve days of culture, dozens of beating colonies of cardiomyocytes were observed in each well of 6-well plates after two weeks of culture. Immunostaining of these cells with 4',6-diamidino-2-phenylindole (DAPI) showed the majority of cells expressed the Troponin I marker (R&D Systems), confirming differentiation into mature cardiomyocytes (FIG. 14G). Fourth, integration-free induced pluripotent stem cells were also differentiated into neuron cells after one month of induction culture (not shown). Finally, qPCR analysis of induced pluripotent stem cells after 10 passages showed that the average copy number of residual episomal vectors decreased to less than 0.01 copy per cell or was undetectable in six out of six induced pluripotent stem cells clones, suggesting that after long-term culture, the episomal vectors were depleted from almost all cells.

Therefore, integration-free induced pluripotent stem cells produced according to the present invention are morphologically, phenotypically and functionally identical to pluripotent stem cells, and can be induced to differentiate into fully functional mesenchymal stem cells, hepatocytes, cardiomyocytes and neurons.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A vector for generating induced pluripotent stem cells from human target cells, the vector comprising:
    a) a vector backbone;
    b) at least two transcription and reprogramming factor genes comprising oct4 and sox2, wherein each gene is separated by a 2a self-cleavage peptide sequence;
    c) a spleen focus-forming virus promoter; and
    d) a post-transcriptional regulatory element Wpre.

2. The vector of claim 1, where the vector backbone is an oriP/EBNA1-based episomal vector.

3. The vector of claim 1, where the vector backbone is an oriP/EBNA1-based plasmid backbone.

4. The vector of claim 1, where the vector is an episomal vector.

5. The vector of claim 1, wherein the at least two transcription and reprogramming factor genes consist of exactly three transcription and reprogramming factor genes, oct4, sox2 and klf4.

6. The vector of claim 1, wherein the at least two transcription and reprogramming factor genes consist of exactly four transcription and reprogramming factor genes, oct4, sox2, klf4 and myc.

7. The vector of claim 1, where the 2a self-cleavage peptide sequence is selected from the group consisting of equine rhinitis A virus, foot-and-mouth disease virus, porcine teschovirus-1 and Thosea asigna virus.

8. The vector of claim 1, further comprising one or more than one anti-apoptotic factor gene encoding one or more than one anti-apoptotic factor selected from the group consisting of BCL-XL and BCL2.

9. A method for generating integration-free induced pluripotent stem cells, the method comprising:
    a) providing hematopoietic target cells;
    b) providing one or more than one vector of claim 1;
    c) transducing or transfecting the hematopoietic target cells with the one or more than one vector; and
    d) culturing the transduced or transfected cells in a cell culture, thereby generating integration-free induced pluripotent stem cells.

10. The method of claim 9, where the one or more than one vector provided is one vector.

11. The method of claim 9, where the one or more than one vector is a first vector and a second vector, and transducing or transfecting the target cells comprises transducing or transfecting the target cells with a first amount of the first vector and a second amount of a second vector, where the first amount is equal to the second amount.

12. The method of claim 9, where the one or more than one vector is a first vector and a second vector, and transducing or transfecting the target cells comprises transducing or transfecting the target cells with a first amount of the first vector and a second amount of a second vector, where the first amount is half of the second amount.

13. The method of claim 9, where the one or more than one vector is an episomal vector comprising a strong spleen focus-forming virus promoter, a post-transcriptional regulatory element Wpre, and exactly two transcription and reprogramming factor genes, oct4 and sox2, and the method further comprises transducing or transfecting the target cells with an additional episomal vector comprising a strong spleen focus-forming virus promoter, a post-transcriptional regulatory element Wpre, an anti-apoptotic factor gene bcl-xl, and exactly one transcription and reprogramming factor gene, klf4.

14. The method of claim 9, where the one or more than one vector is an episomal vector comprising a strong spleen focus-forming virus promoter, a post-transcriptional regulatory element Wpre, and exactly two transcription and reprogramming factor genes, oct4 and sox2, and the method further comprises transducing or transfecting the target cells with a first additional episomal vector comprising a strong spleen focus-forming virus promoter, a post-transcriptional regulatory element Wpre, and exactly one transcription and reprogramming factor gene, klf4, and with a second additional episomal vector comprising a strong spleen focus-forming virus promoter, a post-transcriptional regulatory element Wpre, and an anti-apoptotic factor gene bcl-xl, but without any transcription and reprogramming factor gene.

15. The method of claim 9, further comprising harvesting the target cells from a body fluid or tissue.

16. The method of claim 15, where the body fluid or tissue is peripheral blood.

17. The method of claim 9, further comprising enhancing or purifying the target cells for cells that express a CD33 marker.

18. The method of claim 9, further comprising purifying integration-free induced pluripotent stem cells from the cell culture after generating the integration-free induced pluripotent stem cells.

19. The method of claim 9, further comprising culturing the target cells in a cell culture for a duration of between three days and six days before transducing or transfecting the target cells.

20. The method of claim 9, further comprising culturing the target cells in a cell culture for a duration of four days before transducing or transfecting the target cells.

21. The vector of claim 1, wherein the at least two transcription and reprogramming factor genes further comprise at least one additional transcription and reprogramming factor gene selected from the group consisting of a Yamanaka factor gene, a Thomson/Yu factor gene, klf4, lin28, myc, nanog, oct4, sox1, sox2, sox3, sox15 and sox18, wherein each gene is separated by a 2a self-cleavage peptide sequence.

22. The vector of claim 21, wherein the at least one additional transcription and reprogramming factor genes is selected from klf4 and myc.

23. The vector of claim 1, where the target cells are cord blood cells.

24. The vector of claim 1, where the target cells are peripheral blood cells.

* * * * *